(12) United States Patent
Johnson et al.

(10) Patent No.: US 9,610,091 B2
(45) Date of Patent: *Apr. 4, 2017

(54) ELECTROSURGICAL CUTTING AND SEALING INSTRUMENTS WITH JAWS HAVING A PARALLEL CLOSURE MOTION

(71) Applicant: Ethicon Endo-Surgery, Inc., Cincinnati, OH (US)

(72) Inventors: Gregory W. Johnson, Milford, OH (US); Jeffrey S. Swayze, Hamilton, OH (US); Jason L. Harris, Mason, OH (US); Foster B. Stulen, Mason, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 222 days.

This patent is subject to a terminal disclaimer.

(21) Appl. No.: 14/202,892

(22) Filed: Mar. 10, 2014

(65) Prior Publication Data

US 2014/0194915 A1 Jul. 10, 2014

Related U.S. Application Data

(63) Continuation of application No. 12/758,298, filed on Apr. 12, 2010, now Pat. No. 8,709,035.

(51) Int. Cl.
*A61B 17/00* (2006.01)
*A61B 18/14* (2006.01)
(Continued)

(52) U.S. Cl.
CPC ...... *A61B 17/3205* (2013.01); *A61B 17/2804* (2013.01); *A61B 18/1445* (2013.01);
(Continued)

(58) Field of Classification Search
CPC . A61B 17/2804; A61B 17/3205; A61B 18/04; A61B 18/10; A61B 18/12;
(Continued)

(56) References Cited

U.S. PATENT DOCUMENTS 2,366,274 A 1/1945 Luth et al.
2,458,152 A 1/1949 Eakins
(Continued)

FOREIGN PATENT DOCUMENTS

DE 29623113 U1 10/1997
DE 20004812 U1 9/2000
(Continued)

OTHER PUBLICATIONS

International Search Report and Written Opinion for PCT/US2011/031154, Jul. 6, 2011 (11 pages).
(Continued)

*Primary Examiner* — Michael Peffley
*Assistant Examiner* — Khadijeh Vahdat

(57) ABSTRACT

A surgical instrument comprising an end effector comprising a first jaw member defining a first longitudinal slot, a second jaw member defining a second longitudinal slot, and a first push rod member having a distally directed end pivotably coupled to the first jaw member and a proximally directed end pivotably coupled at a first pivot point. The surgical instrument additionally comprises a reciprocating member translatable distally and proximally through the first and second longitudinal slots, wherein the reciprocating member comprises a blade, a transverse element, and a first shoulder element coupled to and substantially perpendicular to the transverse element. Upon distal motion of the reciprocating member, the first shoulder element contacts the first push rod member to exert a force on at least the first jaw member
(Continued)

causing the first jaw member to translate towards the second jaw member in a substantially parallel motion.

20 Claims, 29 Drawing Sheets

(51) Int. Cl.
*A61B 17/3205* (2006.01)
*A61B 17/28* (2006.01)
*A61B 17/29* (2006.01)

(52) U.S. Cl.
CPC ....... *A61B 18/1447* (2013.01); *A61B 18/1492* (2013.01); *A61B 2017/2933* (2013.01); *A61B 2018/145* (2013.01); *A61B 2018/1412* (2013.01); *A61B 2018/1455* (2013.01)

(58) Field of Classification Search
CPC . A61B 18/1266; A61B 18/14; A61B 18/1442; A61B 18/1445; A61B 18/1447; A61B 18/1492; A61B 2017/2933; A61B 2018/1412; A61B 2018/145; A61B 2018/1455
USPC ............................ 606/51–52, 169, 205–207
See application file for complete search history.

(56) References Cited

U.S. PATENT DOCUMENTS

| | | |
|---|---|---|
| 2,510,693 A | 6/1950 | Green |
| 3,166,971 A | 1/1965 | Stoecker |
| 3,580,841 A | 5/1971 | Cadotte et al. |
| 3,703,651 A | 11/1972 | Blowers |
| 3,777,760 A | 12/1973 | Essner |
| 4,005,714 A | 2/1977 | Hiltebrandt |
| 4,034,762 A | 7/1977 | Cosens et al. |
| 4,058,126 A | 11/1977 | Leveen |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,910,389 A | 3/1990 | Sherman et al. |
| 4,920,978 A | 5/1990 | Colvin |
| 4,936,842 A | 6/1990 | D'Amelio et al. |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,156,633 A * | 10/1992 | Smith .................... A61B 10/06 30/251 |
| 5,160,334 A | 11/1992 | Billings et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,217,460 A | 6/1993 | Knoepfler |
| 5,234,428 A | 8/1993 | Kaufman |
| 5,258,006 A | 11/1993 | Rydell et al. |
| 5,285,945 A | 2/1994 | Brinkerhoff et al. |
| 5,290,286 A | 3/1994 | Parins |
| 5,309,927 A | 5/1994 | Welch |
| 5,318,564 A | 6/1994 | Eggers |
| 5,318,589 A | 6/1994 | Lichtman |
| 5,330,471 A | 7/1994 | Eggers |
| 5,339,723 A | 8/1994 | Huitema |
| 5,342,359 A | 8/1994 | Rydell |
| 5,361,583 A | 11/1994 | Huitema |
| 5,383,874 A | 1/1995 | Jackson et al. |
| 5,387,207 A | 2/1995 | Dyer et al. |
| 5,389,098 A | 2/1995 | Tsuruta et al. |
| 5,395,312 A | 3/1995 | Desai |
| 5,395,363 A | 3/1995 | Billings et al. |
| 5,395,364 A | 3/1995 | Anderhub et al. |
| 5,396,900 A | 3/1995 | Slater et al. |
| 5,403,312 A | 4/1995 | Yates et al. |
| 5,417,709 A | 5/1995 | Slater |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,542,916 A | 8/1996 | Hirsch et al. |
| 5,558,671 A | 9/1996 | Yates |
| 5,563,179 A | 10/1996 | Stone et al. |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,611,813 A | 3/1997 | Lichtman |
| 5,618,307 A | 4/1997 | Donlon et al. |
| 5,624,452 A | 4/1997 | Yates |
| 5,647,871 A | 7/1997 | Levine et al. |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,713,896 A | 2/1998 | Nardella |
| 5,716,366 A | 2/1998 | Yates |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,779,701 A | 7/1998 | McBrayer et al. |
| 5,782,834 A | 7/1998 | Lucey et al. |
| 5,792,138 A | 8/1998 | Shipp |
| 5,797,941 A | 8/1998 | Schulze et al. |
| 5,800,432 A | 9/1998 | Swanson |
| 5,800,449 A | 9/1998 | Wales |
| 5,807,393 A | 9/1998 | Williamson, IV et al. |
| 5,810,811 A | 9/1998 | Yates et al. |
| 5,817,033 A | 10/1998 | DeSantis et al. |
| 5,817,093 A | 10/1998 | Williamson, IV et al. |
| 5,836,909 A | 11/1998 | Cosmescu |
| 5,836,943 A | 11/1998 | Miller, III |
| 5,853,412 A | 12/1998 | Mayenberger |
| 5,876,401 A | 3/1999 | Schulze et al. |
| 5,880,668 A | 3/1999 | Hall |
| 5,891,142 A | 4/1999 | Eggers et al. |
| 5,906,625 A | 5/1999 | Bito et al. |

(56) References Cited

U.S. PATENT DOCUMENTS

| | | |
|---|---|---|
| 5,984,938 A | 11/1999 | Yoon |
| 6,003,517 A | 12/1999 | Sheffield et al. |
| 6,013,052 A | 1/2000 | Durman et al. |
| 6,024,741 A | 2/2000 | Williamson, IV et al. |
| 6,024,744 A | 2/2000 | Kese et al. |
| 6,033,399 A | 3/2000 | Gines |
| 6,039,734 A | 3/2000 | Goble |
| 6,050,996 A | 4/2000 | Schmaltz et al. |
| 6,063,098 A | 5/2000 | Houser et al. |
| 6,068,629 A | 5/2000 | Haissaguerre et al. |
| 6,074,389 A | 6/2000 | Levine et al. |
| 6,091,995 A | 7/2000 | Ingle et al. |
| 6,099,483 A | 8/2000 | Palmer et al. |
| 6,099,550 A | 8/2000 | Yoon |
| H1904 H | 10/2000 | Yates et al. |
| 6,144,402 A | 11/2000 | Norsworthy et al. |
| 6,152,923 A | 11/2000 | Ryan |
| 6,174,309 B1 | 1/2001 | Wrublewski et al. |
| 6,206,876 B1 | 3/2001 | Levine et al. |
| 6,228,080 B1 | 5/2001 | Gines |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,391,026 B1 | 5/2002 | Hung et al. |
| 6,398,779 B1 | 6/2002 | Buysse et al. |
| H2037 H | 7/2002 | Yates et al. |
| 6,419,675 B1 | 7/2002 | Gallo, Sr. |
| 6,430,446 B1 | 8/2002 | Knowlton |
| 6,443,968 B1 | 9/2002 | Holthaus et al. |
| 6,458,128 B1 | 10/2002 | Schulze |
| 6,464,702 B2 | 10/2002 | Schulze et al. |
| 6,491,690 B1 | 12/2002 | Goble et al. |
| 6,500,112 B1 | 12/2002 | Khouri |
| 6,500,176 B1 | 12/2002 | Truckai et al. |
| 6,503,248 B1 | 1/2003 | Levine |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,584,360 B2 | 6/2003 | Francischelli et al. |
| 6,585,735 B1 | 7/2003 | Lands et al. |
| 6,589,200 B1 | 7/2003 | Schwemberger et al. |
| 6,602,252 B2 | 8/2003 | Mollenauer |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,651,669 B1 | 11/2003 | Burnside |
| 6,656,198 B2 | 12/2003 | Tsonton et al. |
| 6,673,248 B2 | 1/2004 | Chowdhury |
| 6,679,882 B1 | 1/2004 | Kornerup |
| 6,695,840 B2 | 2/2004 | Schulze |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,775,575 B2 | 8/2004 | Bommannan et al. |
| 6,789,939 B2 | 9/2004 | Schrödinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,195,631 B2 | 3/2007 | Dumbauld |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,422,139 B2 | 9/2008 | Shelton, IV et al. |
| 7,435,582 B2 | 10/2008 | Zimmermann et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,498,080 B2 | 3/2009 | Tung et al. |
| 7,510,107 B2 | 3/2009 | Timm et al. |
| 7,513,025 B2 | 4/2009 | Fischer |
| 7,517,349 B2 | 4/2009 | Truckai et al. |
| 7,540,872 B2 | 6/2009 | Schechter et al. |

(56) References Cited

U.S. PATENT DOCUMENTS

| | | |
|---|---|---|
| 7,550,216 B2 | 6/2009 | Ofer et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,703,459 B2 | 4/2010 | Saadat et al. |
| 7,708,751 B2 | 5/2010 | Hughes et al. |
| 7,722,607 B2 | 5/2010 | Dumbauld et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,803,156 B2 | 9/2010 | Eder et al. |
| 7,815,641 B2 | 10/2010 | Dodde et al. |
| 7,819,298 B2 | 10/2010 | Hall et al. |
| 7,819,299 B2 | 10/2010 | Sheltoin, IV et al. |
| 7,819,872 B2 | 10/2010 | Johnson et al. |
| 7,832,408 B2 | 11/2010 | Shelton, IV et al. |
| 7,832,612 B2 | 11/2010 | Baxter, III et al. |
| 7,846,159 B2 | 12/2010 | Morrison et al. |
| 7,846,160 B2 | 12/2010 | Payne et al. |
| 7,879,035 B2 | 2/2011 | Garrison et al. |
| 7,879,070 B2 | 2/2011 | Ortiz et al. |
| 7,901,400 B2 | 3/2011 | Wham et al. |
| 7,919,184 B2 | 4/2011 | Mohapatra et al. |
| 7,931,649 B2 | 4/2011 | Couture et al. |
| 7,935,114 B2 | 5/2011 | Takashino et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,058,771 B2 | 11/2011 | Giordano et al. |
| 8,070,036 B1 | 12/2011 | Knodel et al. |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,197,479 B2 | 6/2012 | Olson et al. |
| 8,221,415 B2 | 7/2012 | Francischelli |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |
| 8,277,447 B2 | 10/2012 | Garrison et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,298,232 B2 | 10/2012 | Unger |
| 8,303,583 B2 | 11/2012 | Hosier et al. |
| 8,323,310 B2 | 12/2012 | Kingsley |
| 8,357,158 B2 | 1/2013 | McKenna et al. |
| 8,377,059 B2 | 2/2013 | Deville et al. |
| 8,397,971 B2 | 3/2013 | Yates et al. |
| 8,414,577 B2 | 4/2013 | Boudreaux et al. |
| 8,430,876 B2 | 4/2013 | Kappus et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,486,057 B2 | 7/2013 | Behnke, II |
| 8,496,682 B2 | 7/2013 | Guerra et al. |
| 8,535,311 B2 | 9/2013 | Schall |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| 8,613,383 B2 | 12/2013 | Beckman et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,647,350 B2 | 2/2014 | Mohan et al. |
| 8,663,222 B2 | 3/2014 | Anderson et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,404 B2 | 6/2014 | Boudreaux et al. |
| 8,753,338 B2 | 6/2014 | Widenhouse et al. |
| 8,764,747 B2 | 7/2014 | Cummings et al. |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,834,466 B2 | 9/2014 | Cummings et al. |
| 8,834,518 B2 | 9/2014 | Faller et al. |
| 8,888,776 B2 | 11/2014 | Dietz et al. |
| 8,906,016 B2 | 12/2014 | Boudreaux et al. |
| 8,926,607 B2 | 1/2015 | Norvell et al. |
| 8,926,608 B2 | 1/2015 | Bacher et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,979,843 B2 | 3/2015 | Timm et al. |
| 8,979,844 B2 | 3/2015 | White et al. |
| 8,986,302 B2 | 3/2015 | Aldridge et al. |
| 9,005,199 B2 | 4/2015 | Beckman et al. |
| 9,011,437 B2 | 4/2015 | Woodruff et al. |
| 9,044,243 B2 | 6/2015 | Johnson et al. |
| 9,149,324 B2 | 10/2015 | Huang et al. |
| 9,192,431 B2 | 11/2015 | Woodruff et al. |
| 2002/0022836 A1 | 2/2002 | Goble et al. |
| 2002/0115997 A1* | 8/2002 | Truckai ............. A61B 18/1445 606/51 |
| 2002/0165541 A1 | 11/2002 | Whitman |
| 2003/0014053 A1 | 1/2003 | Nguyen et al. |
| 2003/0105474 A1 | 6/2003 | Bonutti |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1* | 4/2005 | Phan ............. A61B 18/1445 606/41 |

(56) References Cited

U.S. PATENT DOCUMENTS

| | | |
|---|---|---|
| 2005/0131390 A1 | 6/2005 | Heinrich et al. |
| 2005/0165429 A1 | 7/2005 | Douglas et al. |
| 2005/0171522 A1 | 8/2005 | Christopherson |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0173803 A1 | 7/2007 | Wham et al. |
| 2007/0173813 A1 | 7/2007 | Odom |
| 2007/0185474 A1 | 8/2007 | Nahen |
| 2007/0191713 A1 | 8/2007 | Eichmann et al. |
| 2007/0191830 A1 | 8/2007 | Cromton, Jr. et al. |
| 2007/0203483 A1 | 8/2007 | Kim et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0221565 A1 | 9/2008 | Eder et al. |
| 2008/0262491 A1 | 10/2008 | Swoyer et al. |
| 2008/0269862 A1 | 10/2008 | Elmouelhi et al. |
| 2008/0281315 A1 | 11/2008 | Gines |
| 2008/0294158 A1 | 11/2008 | Pappone et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0125026 A1 | 5/2009 | Rioux et al. |
| 2009/0125027 A1 | 5/2009 | Fischer |
| 2009/0138003 A1 | 5/2009 | Deville et al. |
| 2009/0138006 A1 | 5/2009 | Bales et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | Mckenna |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0082486 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0155781 A1 | 6/2011 | Swensgard et al. |
| 2011/0224668 A1 | 9/2011 | Johnson et al. |
| 2011/0276049 A1 | 11/2011 | Gerhardt |
| 2011/0276057 A1 | 11/2011 | Conlon et al. |
| 2011/0301605 A1 | 12/2011 | Horner |
| 2011/0306967 A1 | 12/2011 | Payne et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0109186 A1 | 5/2012 | Parrott et al. |
| 2012/0116379 A1 | 5/2012 | Yates et al. |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0150170 A1 | 6/2012 | Buysse et al. |
| 2012/0172859 A1 | 7/2012 | Condie et al. |
| 2012/0265196 A1 | 10/2012 | Turner et al. |
| 2013/0023875 A1 | 1/2013 | Harris et al. |
| 2013/0023925 A1 | 1/2013 | Mueller |
| 2013/0030433 A1 | 1/2013 | Heard |
| 2013/0079762 A1 | 3/2013 | Twomey et al. |
| 2013/0085496 A1 | 4/2013 | Unger et al. |
| 2013/0103023 A1 | 4/2013 | Monson et al. |
| 2013/0103024 A1 | 4/2013 | Monson et al. |
| 2013/0123776 A1 | 5/2013 | Monson et al. |
| 2013/0123777 A1 | 5/2013 | Monson et al. |
| 2013/0123782 A1 | 5/2013 | Trees et al. |
| 2013/0131660 A1 | 5/2013 | Monson et al. |
| 2013/0253502 A1 | 9/2013 | Aronow et al. |
| 2013/0338661 A1 | 12/2013 | Behnke, II |
| 2014/0005680 A1 | 1/2014 | Shelton, IV et al. |
| 2014/0094801 A1 | 4/2014 | Boudreaux et al. |
| 2014/0148806 A1 | 5/2014 | Witt et al. |
| 2014/0194914 A1 | 7/2014 | Hunt et al. |
| 2014/0257284 A1 | 9/2014 | Artale |
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0066022 A1 | 3/2015 | Shelton, IV et al. |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133915 A1 | 5/2015 | Strobl et al. |
| 2015/0133921 A1 | 5/2015 | Strobl et al. |
| 2015/0190189 A1 | 7/2015 | Yates et al. |
| 2015/0196352 A1 | 7/2015 | Beckman et al. |
| 2015/0201953 A1 | 7/2015 | Strobl et al. |
| 2015/0230853 A1 | 8/2015 | Johnson et al. |
| 2015/0265347 A1 | 9/2015 | Yates et al. |
| 2015/0272602 A1 | 10/2015 | Boudreaux et al. |
| 2015/0272657 A1 | 10/2015 | Yates et al. |
| 2015/0272659 A1 | 10/2015 | Boudreaux et al. |
| 2015/0272660 A1 | 10/2015 | Boudreaux et al. |
| 2015/0289925 A1 | 10/2015 | Voegele et al. |
| 2015/0297286 A1 | 10/2015 | Boudreaux et al. |

FOREIGN PATENT DOCUMENTS

| | | |
|---|---|---|
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0557806 B1 | 5/1998 |
| EP | 0640317 B1 | 9/1999 |

(56) References Cited

FOREIGN PATENT DOCUMENTS

| | | |
|---|---|---|
| EP | 0722696 B1 | 12/2002 |
| EP | 1293172 B1 | 4/2006 |
| EP | 1749479 A1 | 2/2007 |
| EP | 1767157 A1 | 3/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1728475 B1 | 8/2011 |
| EP | 2353518 A1 | 8/2011 |
| EP | 2508143 B1 | 2/2014 |
| GB | 2472216 A | 2/2011 |
| JP | H 08-229050 A | 9/1996 |
| JP | 2008-018226 A | 1/2008 |
| WO | WO 81/03272 A1 | 11/1981 |
| WO | WO 93/07817 A1 | 4/1993 |
| WO | WO 93/22973 A1 | 11/1993 |
| WO | WO 95/10978 A1 | 4/1995 |
| WO | WO 96/35382 A1 | 11/1996 |
| WO | WO 97/10764 A1 | 3/1997 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40861 A1 | 8/1999 |
| WO | WO 00/24330 A1 | 5/2000 |
| WO | WO 00/24331 A1 | 5/2000 |
| WO | WO 00/25691 A1 | 5/2000 |
| WO | WO 01/28444 A1 | 4/2001 |
| WO | WO 02/080797 A1 | 10/2002 |
| WO | WO 03/001986 A1 | 1/2003 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2004/078051 A2 | 9/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/084768 A1 | 7/2011 |
| WO | WO 2011/089717 A1 | 7/2011 |
| WO | WO 2011/144911 A1 | 11/2011 |
| WO | WO 2013/034629 A1 | 3/2013 |
| WO | WO 2013/062978 A2 | 5/2013 |
| WO | WO 2013/154157 A1 | 10/2013 |

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Hörmann et al., "Reversible and irreversible denaturation of collagen fibers." Biochemistry, 10, pp. 932-937 (1971).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-induced changes in the mechanics of a collagenous tissue: pseudoelastic behavior at 37° C.," Journal of Biomechanics, 31, pp. 211-216 (1998).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

Kurt Gieck & Reiner Gieck, *Engineering Formulas* § Z.7 (7th ed. 1997).

National Semiconductors Temperature Sensor Handbook—http://www.national.com/appinfo/tempsensors/files/temphb.pdf; accessed online: Apr. 1, 2011.

Glaser and Subak-Sharpe, *Integrated Circuit Engineering*, Addison-Wesley Publishing, Reading, MA (1979).

Wright, et al., "Time-Temperature Equivalence of Heat-Induced Changes in Cells and Proteins," Feb. 1998. ASME Journal of Biomechanical Engineering, vol. 120, pp. 22-26.

Covidien Brochure, [Value Analysis Brief], LigaSure Advance™ Pistol Grip, dated Rev. Apr. 2010 (7 pages).

(56) References Cited

OTHER PUBLICATIONS

Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Covidien Brochure, The LigaSure Precise™ Instrument, dated Mar. 2011 (2 pages).
Erbe Electrosurgery VIO® S, (2012), p. 7, 12 pages, accessed Mar. 31, 2014 at http://www.erbe-med.com/erbe/media/Marketingmaterialien/85140-170_ERBE_EN_VIO_200_S_D027541.
Jang, J. et al. "Neuro-fuzzy and Soft Computing." Prentice Hall, 1997, pp. 13-89, 199-293, 335-393,453-496, 535-549.
Douglas, S.C. "Introduction to Adaptive Filter". Digital Signal Processing Handbook. Ed. Vijay K. Madisetti and Douglas B. Williams. Boca Raton: CRC Press LLC, 1999.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.

\* cited by examiner

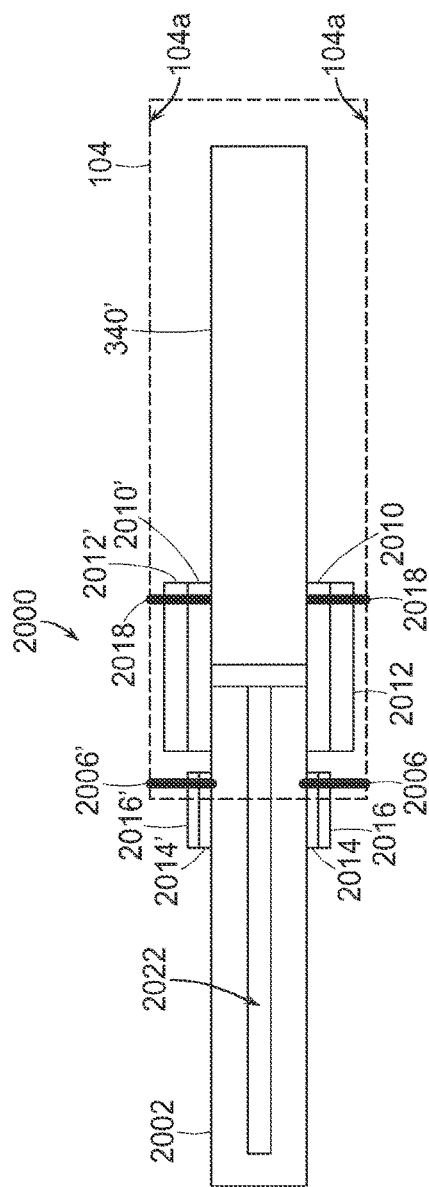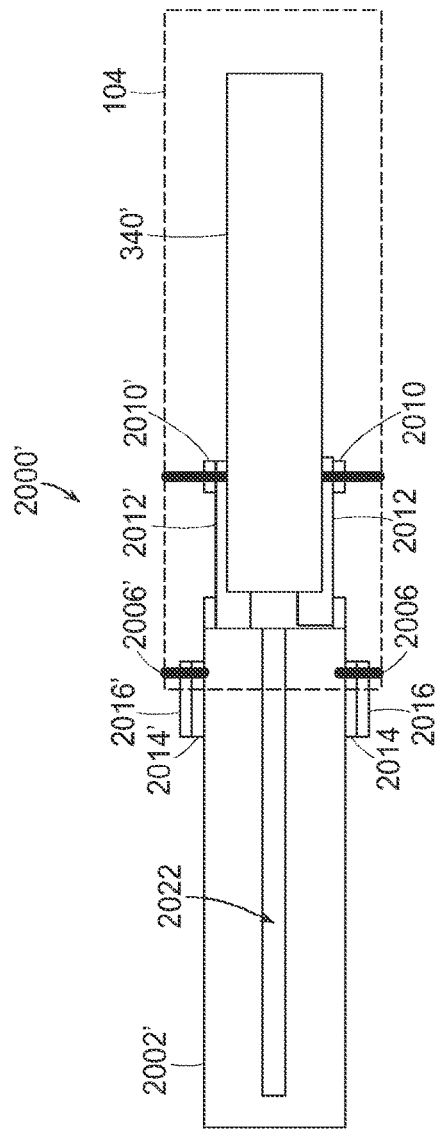
FIG. 22
FIG. 23

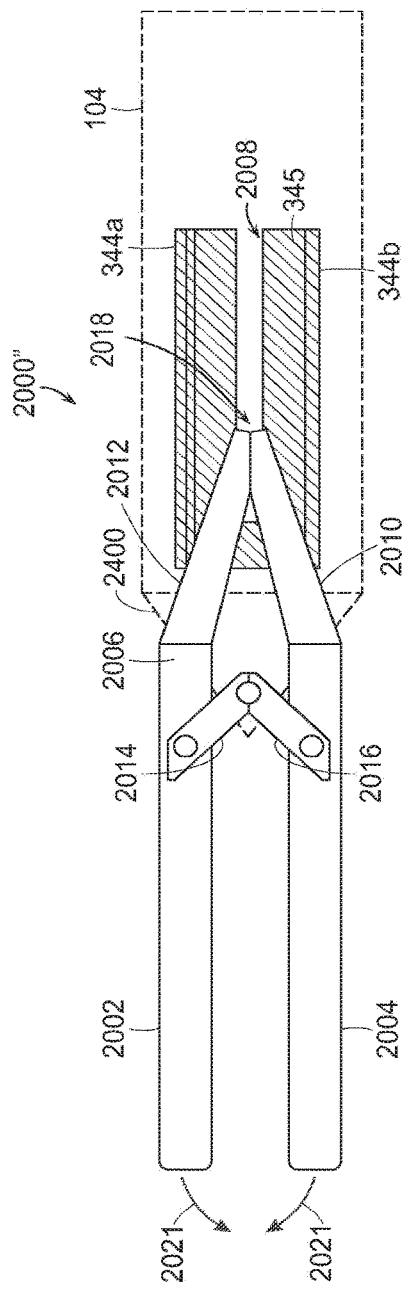
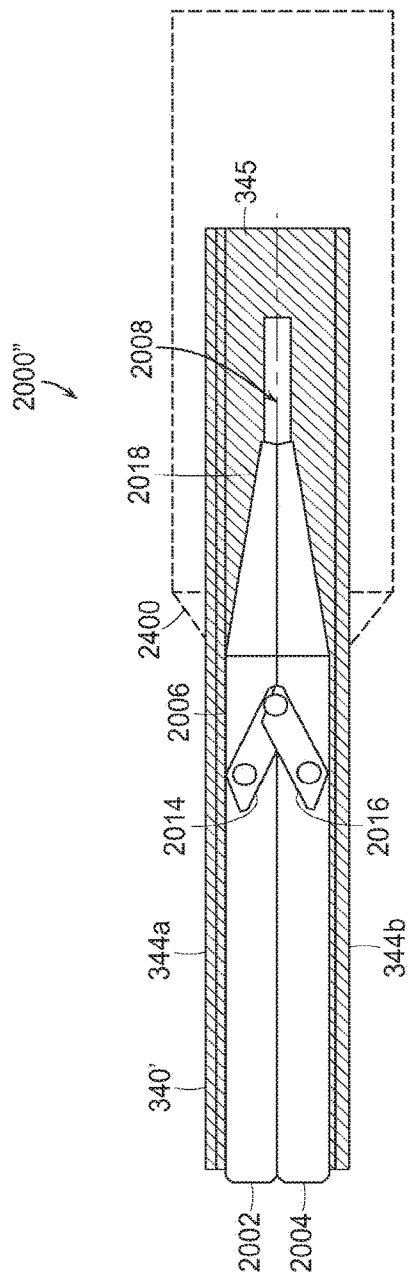
FIG. 24
FIG. 25

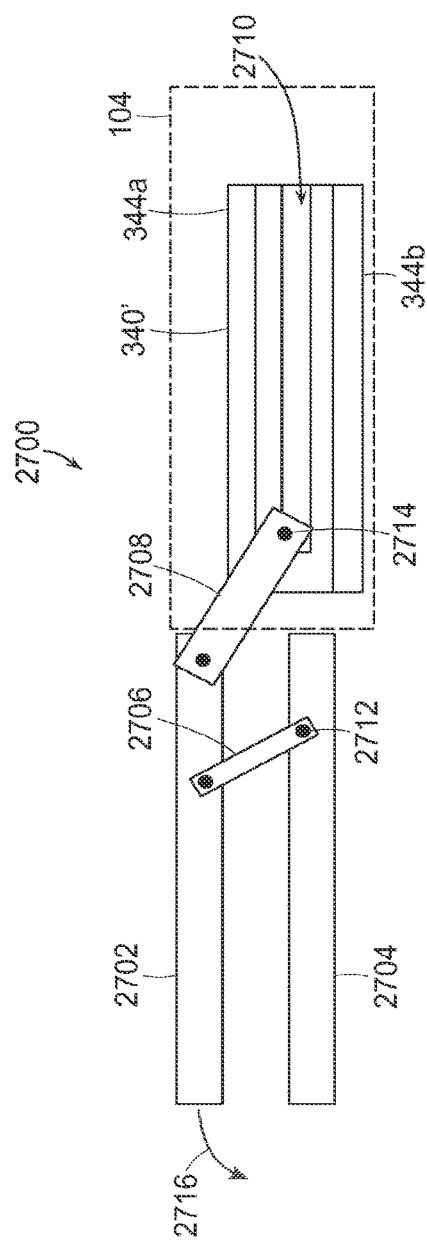
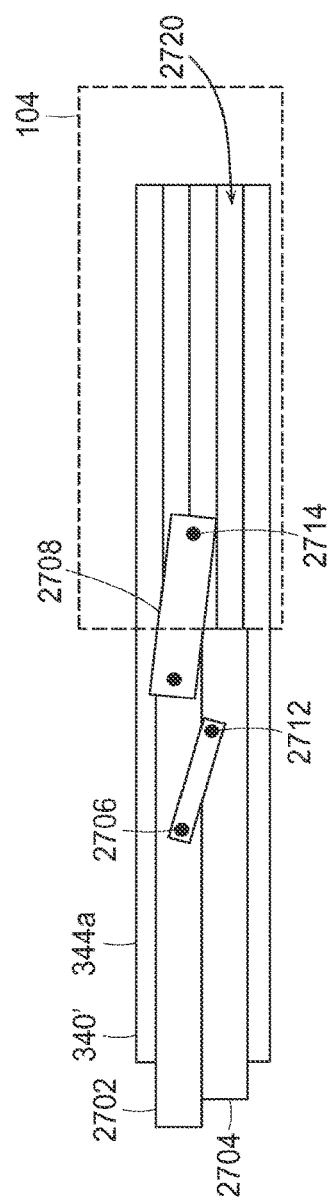
FIG. 26
FIG. 27

ELECTROSURGICAL CUTTING AND SEALING INSTRUMENTS WITH JAWS HAVING A PARALLEL CLOSURE MOTION

This application is a continuation application claiming priority under 35 U.S.C. §120 to U.S. patent application Ser. No. 12/758,298, entitled ELECTROSURGICAL CUTTING AND SEALING INSTRUMENTS WITH JAWS HAVING A PARALLEL CLOSURE MOTION, now U.S. Pat. No. 8,709,035, filed on Apr. 12, 2010, which is incorporated herein by reference in its entirety.

BACKGROUND

Various embodiments are directed to electrosurgical cutting and sealing instruments with jaws having a parallel closure motion that may be used, for example, in open and minimally invasive surgical environments.

Minimally invasive procedures are desirable because such procedures can reduce pain and provide relatively quick recovery times as compared to conventional open medical procedures. Many minimally invasive procedures are performed with an endoscope (including without limitation laparoscopes). Such procedures permit a physician to position, manipulate, and view medical instruments and accessories inside the patient through a small access opening in the patient's body. Laparoscopy is a term used to describe such an "endosurgical" approach using an endoscope (often a rigid laparoscope). In this type of procedure, accessory devices (such as end effectors for creating energy-induced tissue welds) are inserted into a patient through trocars placed through the body wall. Still less invasive treatments include those that are performed through insertion of an endoscope through a natural body orifice to a treatment region. Examples of this approach include, but are not limited to, cystoscopy, hysteroscopy, esophagogastroduodenoscopy, and colonoscopy.

Many of these procedures employ a flexible endoscope during the procedure. Flexible endoscopes often have a flexible, steerable articulating section near the distal end that can be controlled by the clinician by utilizing controls at the proximal end. Some flexible endoscopes are relatively small (1mm to 3mm in diameter), and may have no integral accessory channel (also called biopsy channels or working channels). Other flexible endoscopes, including gastroscopes and colonoscopes, have integral working channels having a diameter of about 2.0 to 3.7 mm for the purpose of introducing and removing medical devices and other accessory devices to perform diagnosis or therapy within the patient. For example, some end effectors are used to create an energy-induced weld or seal. Certain specialized endoscopes or steerable overtubes are available, such as large working channel endoscopes having a working channel of 5 mm, or larger, in diameter, which can be used to pass relatively large accessories, or to provide capability to suction large blood clots. Other specialized endoscopes include those having two or more working channels.

A common task both in minimally invasive and open surgical environments is to grasp, cut and fasten tissue while leaving the cut ends hemostatic (e.g., not bleeding). For example, it is often desirable to cut and seal bodily lumens, such as individual blood vessels or tissue including various vasculature. When sealing a fluid-carrying bodily lumen, it is often necessary for the seal to have sufficient strength to prevent leakage of the fluid, which may exert considerable fluid pressure.

Instruments exist for simultaneously making a longitudinal incision in tissue and fastening the tissue on opposing sides of the incision. Such instruments commonly include an end effector having a pair of cooperating jaw members that, if the instrument is intended for minimally invasive applications, are capable of passing through a cannula passageway or endoscopic working channel. In use, the clinician is able to close the jaw members to clamp the tissue to be cut. A reciprocating cutting instrument (or knife) is drawn distally along the jaw members to transect the clamped tissue. Simultaneously, a fastening mechanism fastens the cut ends of the tissue on opposing sides of the incision. Known fastening mechanisms include staples, sutures or various instruments utilizing energy sources. For example, various energy sources such as radio frequency (RF) sources, ultrasound sources and lasers have been developed to coagulate, seal or join together tissue volumes.

SUMMARY

Various embodiments are directed to a surgical instrument comprising a handle a shaft, an end effector and a reciprocating member. The shaft may be coupled to the handle and may extend distally along a longitudinal axis. The end effector may be positioned at a distal end of the shaft and may comprise first and second jaw members, first and second push rod members, as well as first and second linkage members. The first and second jaw members may, respectively, define first and second longitudinal slots. The first push rod member may have a distally directed end pivotably coupled to the first jaw member and a proximally directed end pivotably coupled to the shaft at a first pivot point. The second push rod member may have a distally directed end pivotably coupled to the second jaw member and a proximally directed end pivotably coupled to the shaft at the first pivot point. The first linkage member may have a distally directed end pivotably coupled to the first jaw member and a proximally directed end pivotably coupled to a second pivot point. The second linkage member may have a distally directed end pivotably coupled to the second jaw member and a proximally directed end pivotably coupled to the second pivot point. The reciprocating member may be translatable distally and proximally parallel to the longitudinal axis through the first longitudinal slot and the second longitudinal slot. A distal portion of the reciprocating member may define a blade. Distal motion of the reciprocating member may exert a force on the first and second jaw members causing the first and second jaw members to translate towards one another in a substantially parallel motion.

Various embodiments may be directed to a surgical instrument comprising a handle, a shaft, an end effector and a reciprocating member. The shaft may be coupled to the handle and extending distally along a longitudinal axis. The end effector may be positioned at a distal end of the shaft, and may comprise first and second jaw members, a first push rod member and a first linkage member. The first and second jaw members may, respectively, define first and second longitudinal slots. The second jaw member may be coupled to the shaft. The first push rod member may have a distally directed end pivotably coupled to the first jaw member and a proximally directed end pivotably coupled to at least one of the shaft and the second jaw at a first pivot point. The first linkage member may have a distally directed end pivotably coupled to the first jaw member and a proximally directed end pivotably coupled to at least one of the shaft and the second jaw at a second pivot point. The reciprocating member may be translatable distally and proximally parallel to the longitudinal axis through the first longitudinal slot and the second longitudinal slot. The distal portion of the reciprocating member may define a blade. Distal motion of the reciprocating member may exert a force on the first and second jaw members causing the first jaw member to translate towards the second jaw member in a substantially parallel motion.

FIGURES

Various features of the embodiments described herein are set forth with particularity in the appended claims. The various embodiments, however, both as to organization and methods of operation may be understood in accordance with the following description taken in conjunction with the accompanying drawings as follows.

FIG. 22 illustrates a top view of one embodiment of the end effector of FIG. 20.

FIG. 23 illustrates a top view of one embodiment of the end effector of FIG. 22 according to an alternate arrangement.

FIGS. 24 and 25 illustrate one embodiment of an end effector of FIG. 20 mounted to the shaft via a clevis.

FIGS. 26 and 27 illustrate one embodiment of an end effector having a single movable jaw member.

DESCRIPTION

Various embodiments are directed to electrosurgical devices for cutting and sealing, for example, cutting and sealing a bodily lumen. According to various embodiments, the electrosurgical devices may comprise an end effector having a pair of jaw members with a parallel closing motion. For example, substanially all of each jaw member may translate through the same distance to reach the closed position. Also, for example, the angular orientation of the jaw members relative to one another may be the same when the jaw member is in the open position as when the jaw member is in the closed position. Accordingly, "milking" of tissue towards the distal end of the end effector may be minimized. This may promote a more even distribution of tissue between the jaw members, enhancing the efficiency of the cutting and/or sealing mechanism. Also, it may prevent situations where portions of the tissue "milk" out the distal end of the end effector and are, therefore, not cut or sealed.

Figure 1:
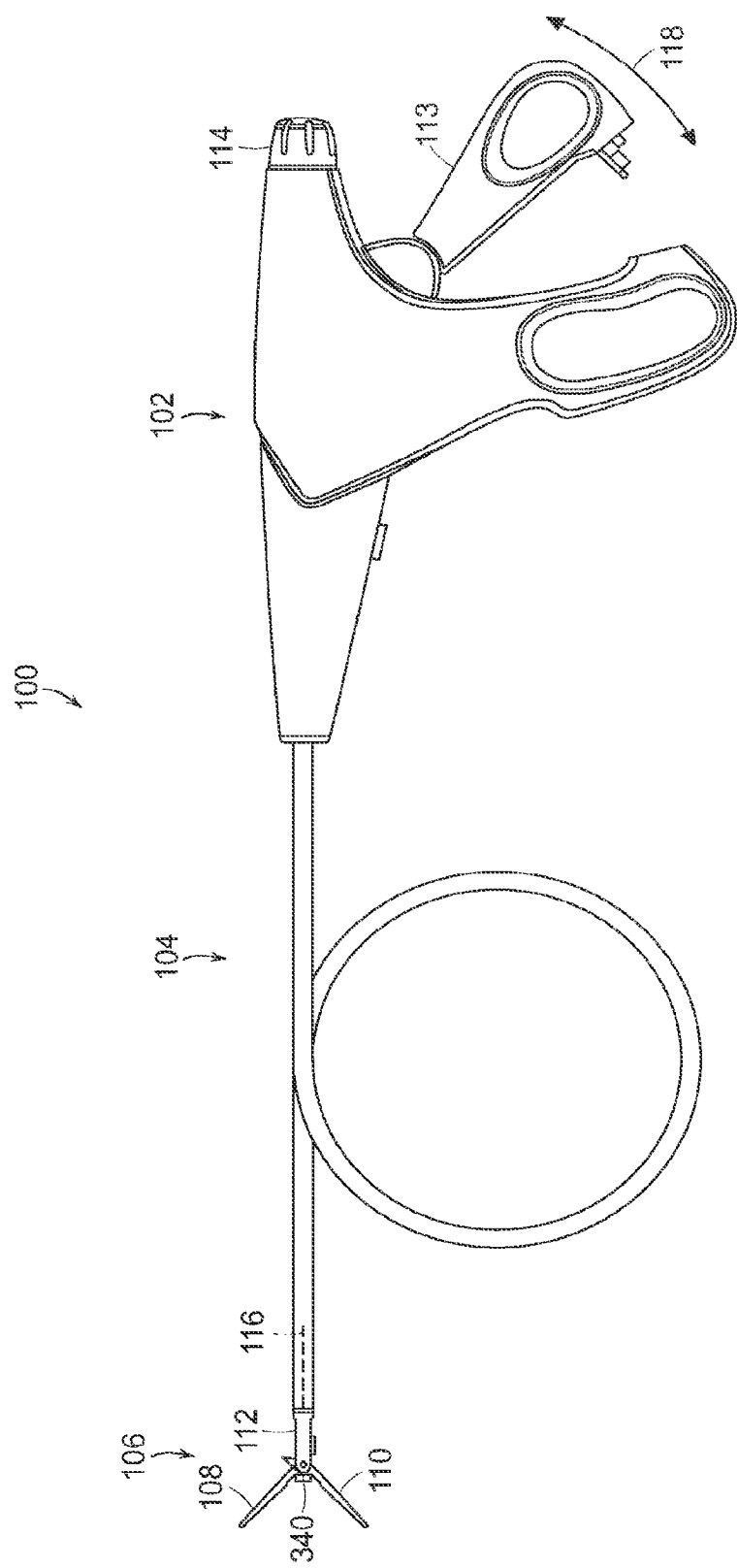
FIG. 1 illustrates one embodiment of a transection and sealing instrument, which may be used, for example, with an endoscope.

FIG. 1 illustrates one embodiment of a transection and sealing instrument 100. The instrument 100 may be used with an endoscope, laparoscope, or any other suitable introduction device. According to various embodiments, the transection and sealing instrument 100 may comprise a handle assembly 102, a shaft 104 and an end effector 106. The shaft 104 may be rigid (e.g., for laparoscopic application and/or open surgical application) or flexible, as shown, (e.g., for endoscopic application). In various embodiments, the shaft 104 may comprise one or more articulation points (e.g., in embodiments where the shaft 104 is rigid). The end effector 106 may comprise a first jaw member 108 and a second jaw member 110. The first jaw member 108 and second jaw member 110 may be connected to a clevis 112, which, in turn, may be coupled to the shaft 104. In various embodiments, as illustrated below, the jaw members 108, 110 may be directly coupled to the shaft 104 and the clevis 112 may be omitted. Also, for example, the jaw members 108, 110 may be coupled to the shaft via one or more push rods or other linkage devices (not shown in FIG. 1). In FIG. 1, the end effector 106 is shown with the jaw members 108, 110 in an open position. A reciprocating blade/I-beam member 340 is illustrated between the jaw members 108, 110.

Figure 2:
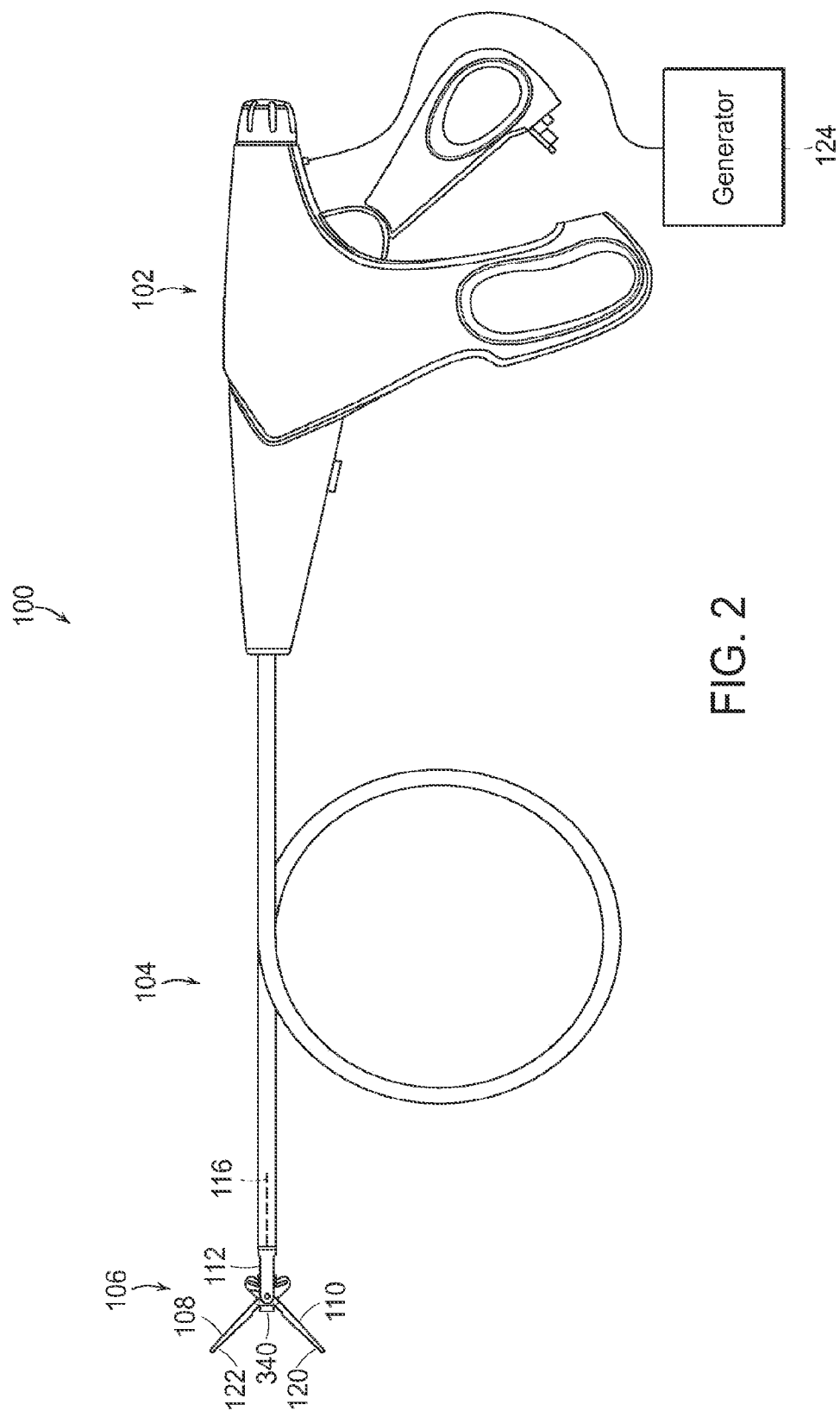
FIG. 2 illustrates one embodiment of the transection and sealing instrument of FIG. 1 for use in electrosurgical applications.

According to various embodiments, one or both of the jaw members 108, 110 may include, or serve as electrodes in monopolar or bi-polar electrosurgical applications including, for example, cutting, coagulation and welding. FIG. 2 illustrates one embodiment of the transection and sealing instrument 100 for use in electrosurgical applications. The jaw members 108, 110 of the end effector 106 may comprise respective electrodes 120, 122. The electrodes 120, 122 may be connected to an electrosurgical generator 124 via wires (not shown) extending from the end effector 106 through the shaft 104 and handle 102. The generator 124 may generate any suitable type of signal for electrosurgical applications. For example, the generator 124 may make various alternating current (A/C) and/or direct current (D/C) signals at suitable voltages, currents, frequencies and wave patterns. According to various embodiments, the transection and sealing instrument 100 may be configured for monopolar operation. In this case, the end effector 106 may comprise a single electrode, rather than two. According to various embodiments, all or a portion of the end effector 106 may serve as the single electrode.

A translating member 116 may extend within the shaft 104 from the end effector 106 to the handle 102. The translating member 116 may be made from any suitable material. For example, the translating member 116 may be, a metal wire (e.g., a tri-layered steel cable), a plastic or metal shaft, etc. In some embodiments, one or more additional translating members (not shown in FIG. 2) may be included to control the motion of the end effector 106 and/or the shaft 104. In various embodiments, the instrument 100 may comprise multiple translating members 116, for example, as described below. At the handle 102, the shaft 104 may be directly or indirectly coupled to an actuator 113 (FIG. 1). In use, a clinician may cause the actuator 113 to pivot along arrow 118 from a first position to a second position. When the actuator moves from the first position to the second position, it may translate the translating member 116 distally or proximally. Distal or proximal motion of the translating member 116 may, in turn, cause the end effector 106 to transition from an open position to a closed position (or vice versa) and/or to perform various other surgical activities such as, for example, severing and/or joining or welding. According to various embodiments, the handle 102 may comprise multiple actuators 113. When multiple actuators 113 are present, each actuator 113 may be used by a clinician to cause the end effector 106 to perform different surgical activities. In various embodiments a single actuator 113 may cause the end effector 106 to perform more than one activity. For example, a clinician may activate a single actuator 113 to force a reciprocating member 340 distally. This may, as described, both close the jaw members 108, 110 and transect any tissue between the jaw members 108, 110.

Figure 3:
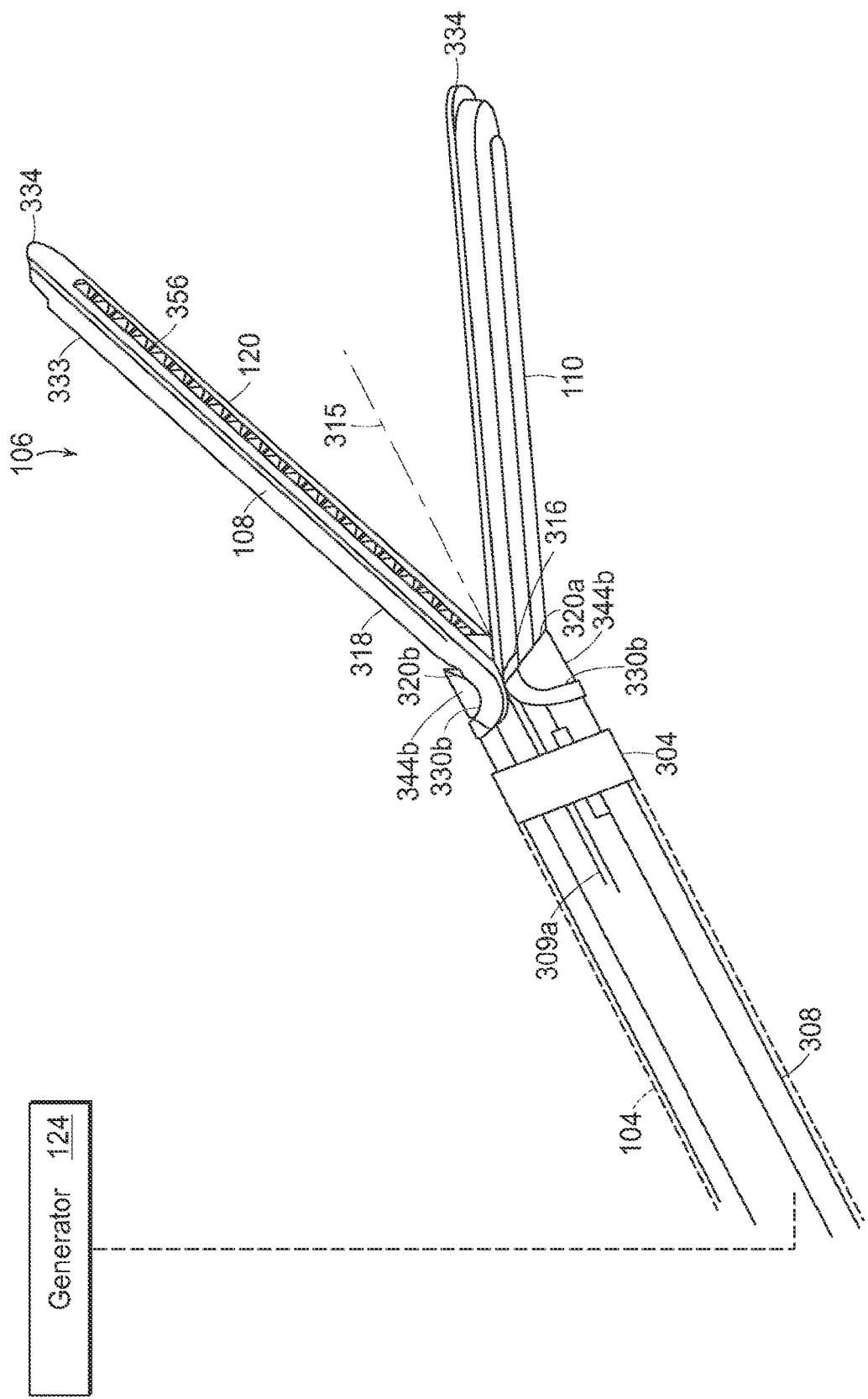
FIGS. 3 and 4 illustrate one embodiment of an end effector of a surgical grasping instrument adapted for transecting captured tissue and contemporaneous sealing of the captured tissue with RF energy delivery.
Figure 4:
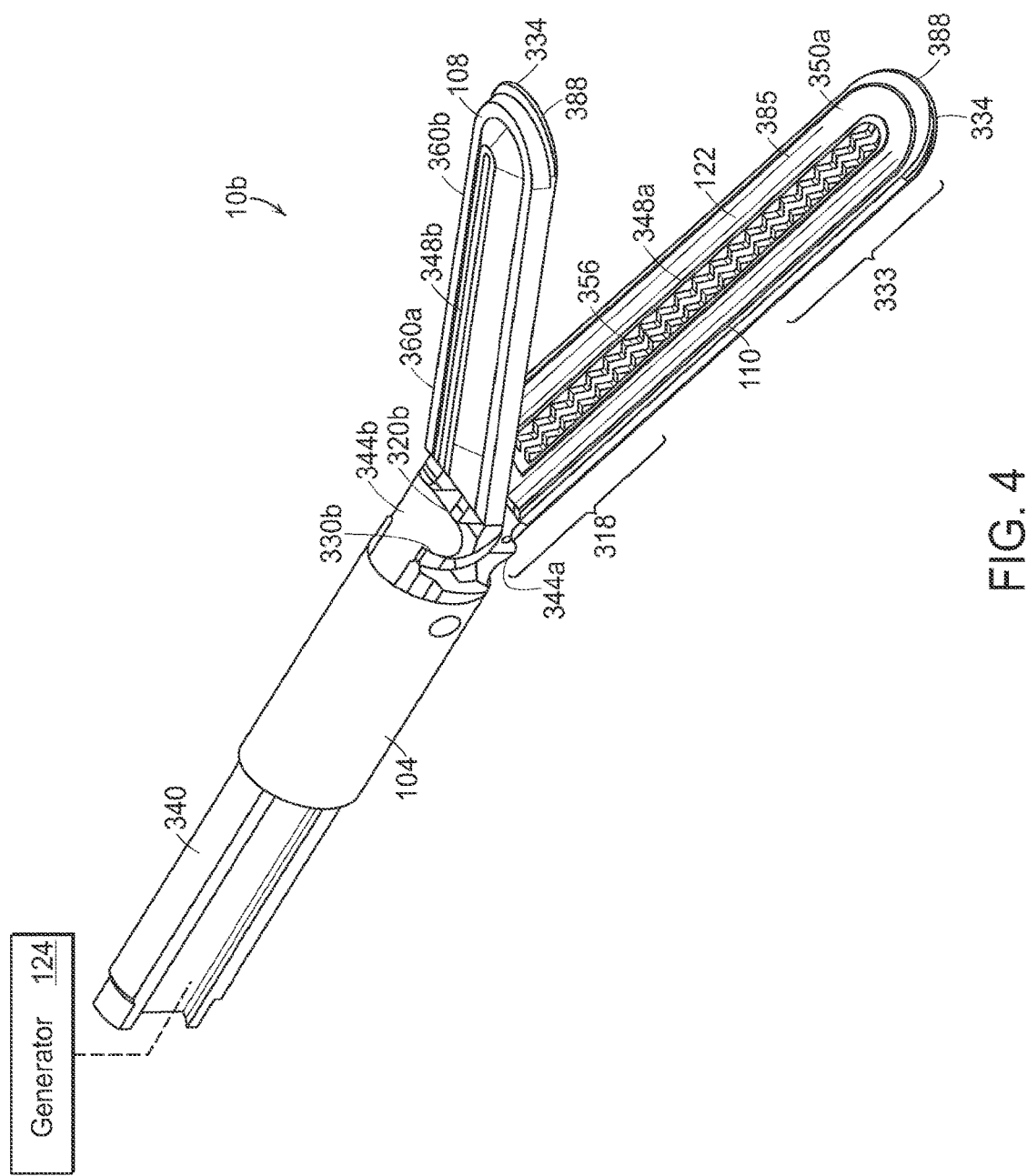

FIGS. 3 and 4 illustrate one embodiment of an end effector 106 of the instrument 100 adapted for transecting captured tissue and contemporaneous sealing of the captured tissue with RF energy delivery. The end effector 106 is carried at the distal end 304 of the shaft 104 that can be rigid, articulatable or deflectable in any suitable diameter. For example, the shaft 104 can have a diameter ranging from about 2 mm to 20 mm to cooperate with cannulae in endoscopic/laparoscopic surgeries or for use in open surgical procedures. The shaft 104 extends from a proximal handle, such as the handle 102. The handle 102 can be any type of pistol-grip or other type of handle known in the art that carries actuator levers, triggers or sliders for moving the translating member 116 or members distally and proximally to actuate the jaws as will be disclosed below. The shaft 104 has a bore 308 extending therethrough for carrying actuator mechanisms (e.g., translating member 116) for actuating the jaws and for carrying electrical leads 309a-309b for the electrosurgical components of the end effector 106.

FIGS. 3 and 4 show details of the end effector 106, including the (upper) jaw element 108 and (lower) jaw element 110 that are adapted to close or approximate along an axis 315. The jaw elements 108, 110 may both be moveable or a single jaw may rotate to provide the open and closed positions. In the example embodiment of FIGS. 1 and 2, both the lower and upper jaws 110, 108 are moveable relative to a rolling pivot location 316 defined further below.

An opening-closing mechanism of the end effector 106 operates on the basis of cam mechanisms that provide a positive engagement of camming surfaces both distal and proximal to a pivoting location (i) for moving the jaw assembly to the (second) closed position to engage tissue under very high compressive forces, and (ii) for moving the jaws toward the (first) open position to apply substantially high opening forces for "dissecting" tissue. This feature allows the surgeon to insert the tip of the closed jaws into a dissectable tissue plane—and thereafter open the jaws to apply such dissecting forces against the tissues.

Figure 5:
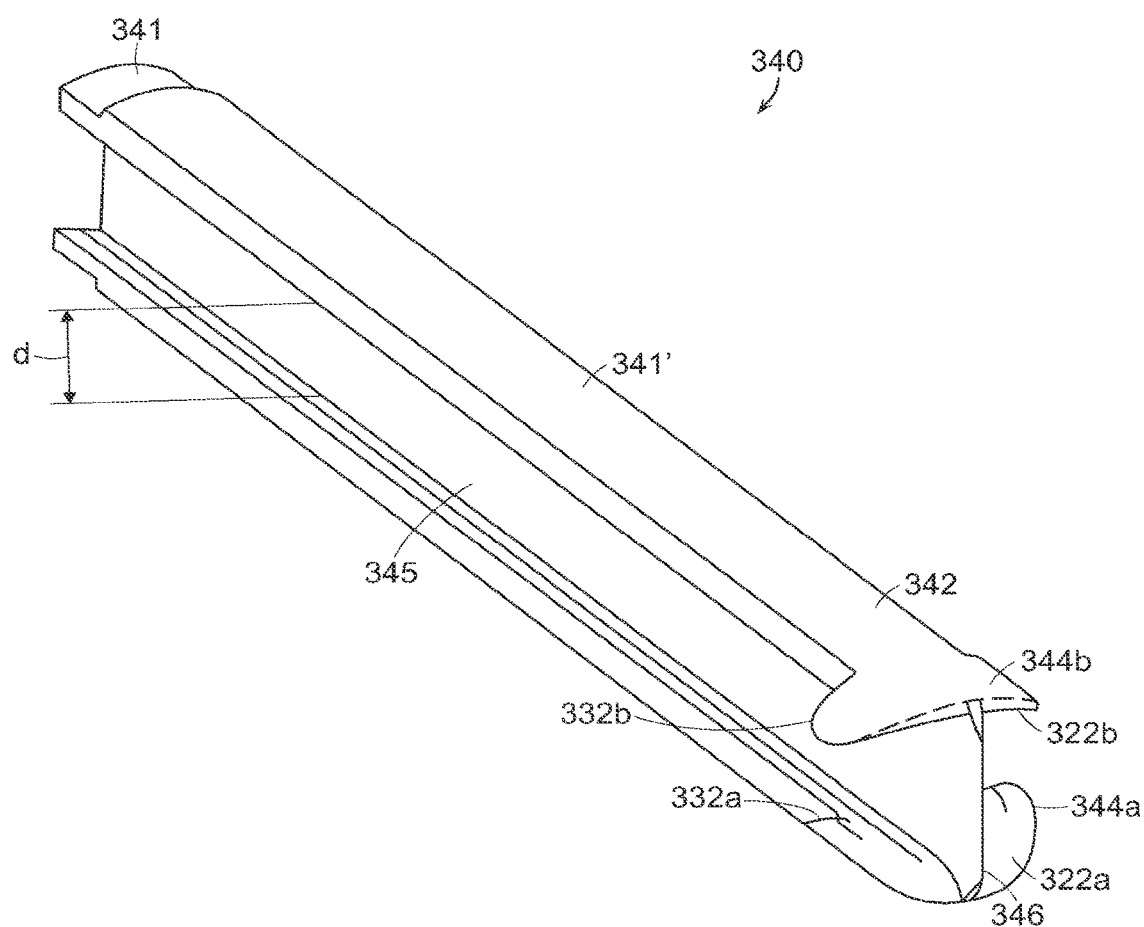
FIGS. 5 and 6 illustrate one embodiment of the reciprocating member shown in FIGS. 3 and 4.
Figure 6:
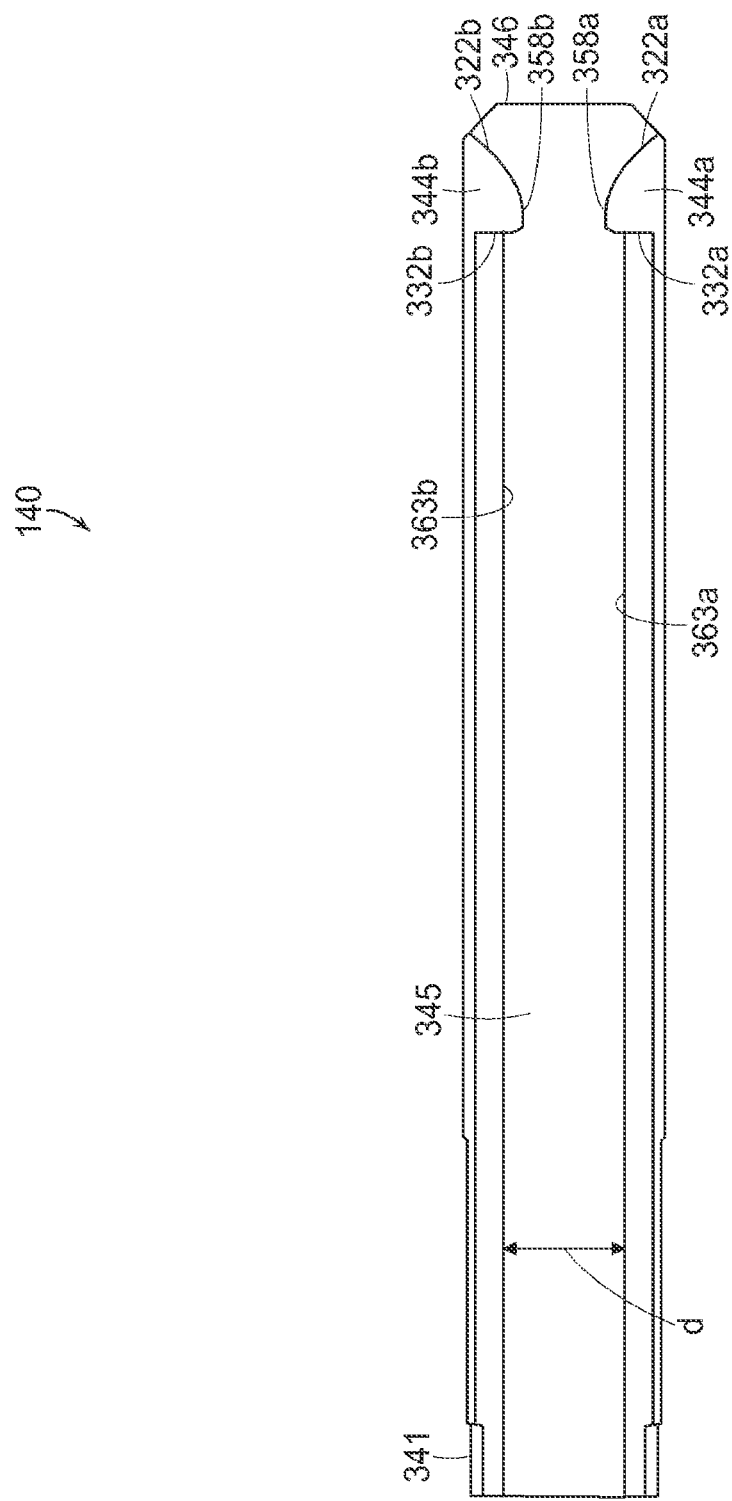

According to various embodiments, the lower and upper jaws 110, 108 may have a first end 318, in the open position, that defines first (proximally-facing) arcuate outer surface portions indicated at 320a and 320b that are engaged by a first surface portions 322a and 322b of a reciprocating I-beam member 340 (FIG. 4) that is adapted to slide over the jaw elements 108, 110 to thereby move the jaws toward closed position. FIGS. 5 and 6 show views that illustrate the cam surfaces of reciprocating member 340 de-mated from jaws 110 and 108. The first end portion 318 of the lower and upper jaws, in the open position, further defines second (distally-facing) arcuate surface portions indicated at 330a and 330b that are engaged by second surface portions 332a and 332b (FIG. 5) of the reciprocating member 340 for moving the jaw elements to the open position. The effective point of jaw rotation may lie between the first and second arcuate cam surfaces of the jaws. The distal (second) end region 333 of the paired jaws is rounded with a lip 334 that can serve as an electrode for surface coagulation as will be described below.

In this embodiment of FIGS. 3, 4 and 5, the reciprocating member 340 may be actuatable from the handle of the instrument by any suitable mechanism, such as actuator 113. For example, the actuator 113 may be coupled to a proximal end 341 of the member 340 and/or may be coupled to a translating member or members 116 that are, in turn, coupled to the reciprocating member. The proximal end 341 and medial portion 341' of member 340 are dimensioned to reciprocate within bore 308 of the shaft 104. The distal portion 342 of reciprocating member 340 carries first (lower) and second (upper) laterally-extending flanges or shoulder elements 344A and 344B that are coupled by an intermediate transverse element 345. The transverse element 345 further is adapted to transect tissue captured between the jaws with a leading edge 346 (FIG. 5) that can be a blade or a cutting electrode. The transverse element 345 is adapted to slide within channels 348a and 348b in the paired first and second jaws 110, 108. As can be seen best in FIGS. 5 and 6, the laterally-extending shoulder elements 344A and 344B define the surfaces 322a, 322b, 332a, 332b that slidably engage the arcuate cam surfaces of the jaws and that apply high compressive forces to the jaws in the closed position.

According to various embodiments, the first and second jaws 108 and 110 may define tissue-engaging surfaces or planes 350a and 350b that contact and deliver energy to engaged tissues, in part, from RF electrodes 120, 122. The engagement plane 350a of the lower jaw 110 may be adapted to deliver energy to tissue, and the tissue-contacting surface 350b of upper jaw 108 may be electrosurgically active or passive as will be described below. Alternatively, the engagement surfaces 350a, 350b of the jaws can carry any suitable electrode arrangement known in the art.

The jaws 108, 110 may have teeth or serrations 356 in any location for gripping tissue. The embodiment of FIGS. 3 and 4 depicts such serrations 356 at an inner portion of the jaws along channels 348a and 348b thus leaving engagement planes 350a and 350b laterally outward of the tissue-gripping elements. The serrations 356 may be of any suitable symmetric or asymmetric shape or combination of shapes including, for example, triangular, rounded, sinusoidal, etc. In the embodiments described below, the engagement planes 350a and 350b and electrode(s) 120, 122 generally are shown with a non-serrated surface for clarity of explanation, but such engagement planes and electrodes themselves can be any non-smooth gripping surface. The axial length of jaws 108, 110 indicated at L can be any suitable length depending on the anatomic structure targeted for transection and sealing. In various embodiments, the length L may be between 10 mm and 50 mm. In some embodiments, the length L may be longer. For example, one embodiment of an end effector 106 for resecting and sealing organs such as a lung or liver may have a length L of about 200 mm. Also, for example, for some surgical tasks, the jaws having a shorter length L may be used, including, for example, jaws having a length L of about 5.0 mm.

Figure 9:
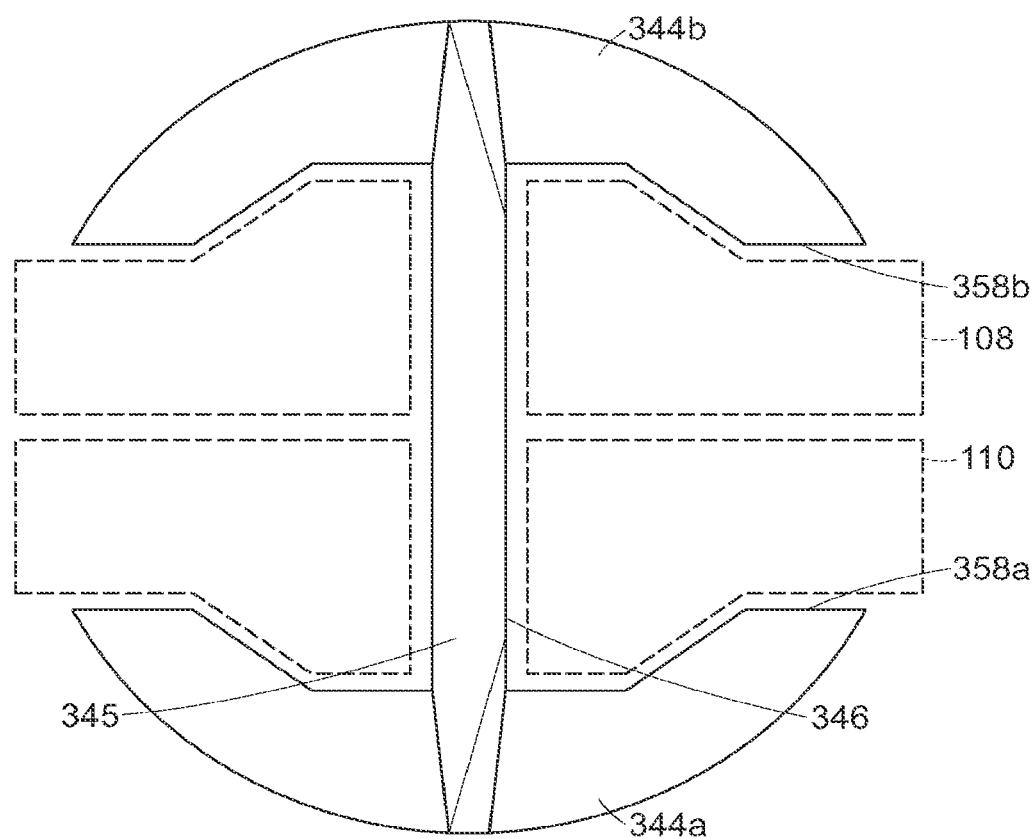
FIG. 9 illustrates an end view of one embodiment of the reciprocating member of FIG. 3 with the jaws of the end effector in phantom view.
Figure 10:
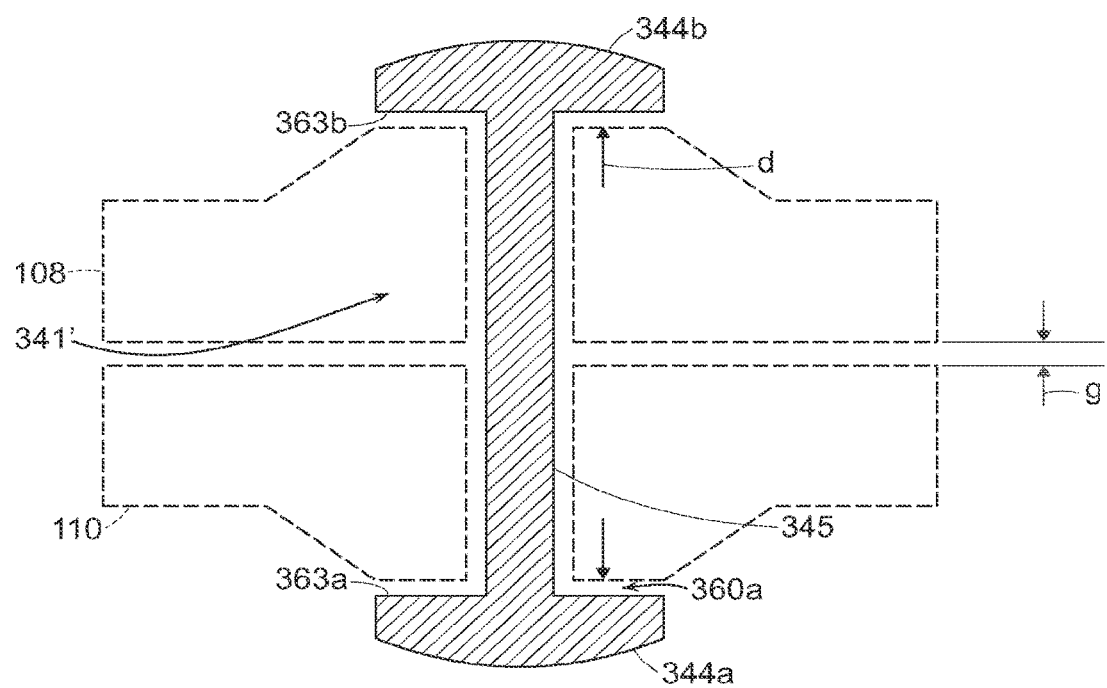
FIG. 10 illustrates a cross-sectional view of the embodiment shown in FIG. 9 along a cross-section taken at a position proximally located from the end view shown in FIG. 9.

FIG. 9 illustrates an end view of one embodiment of the reciprocating member 340 with the jaws 110 and 108 in phantom view. The view shown in FIG. 9 is a head-on view with the distally positioned blade surface 346 pointed out of the page. FIG. 10 illustrates a cross-sectional view of the embodiment shown in FIG. 9 along a cross-section taken at a position proximally located from the end view shown in FIG. 9. The transverse element 345 of the reciprocating member 340 may define a transverse dimension d between innermost surfaces 358a and 358b of the flanges 344A, 344B of the reciprocating member 340 and cooperating medial and distal outer surfaces 360A and 360B of the jaws. The selected transverse dimension d between the flanges or shoulders 344A and 344B thus further defines the engagement gap g between the engagement planes 350a and 350b of the jaws in the closed position. It has been found that very high compression of tissue combined with controlled RF energy delivery is optimal for welding the engaged tissue volume contemporaneous with transection of the tissue. According to various embodiments, the engagement gap g between the engagement planes 350a, 350b may range from about 0.001" to about 0.050". For example, the gap g between the engagement planes ranges from about 0.001" to about 0.010". As can be seen in FIGS. 5 and 10, the medial portion 341' of the reciprocating member 340 may have an "I"-beam shape with inner surface portions 363a and 363b that engage the cooperating medial outer surfaces of the jaws. Thus, in various embodiments, the entire length L of the jaws can be maintained in a fixed spaced-apart relationship to define a consistent engagement gap g. According to various embodiments, the engagement gap g may be selected to be large enough to prevent tissue engaged between the jaws 108, 110 from being sheared and to prevent electrical shorts between the electrodes 120, 122.

Figure 7:
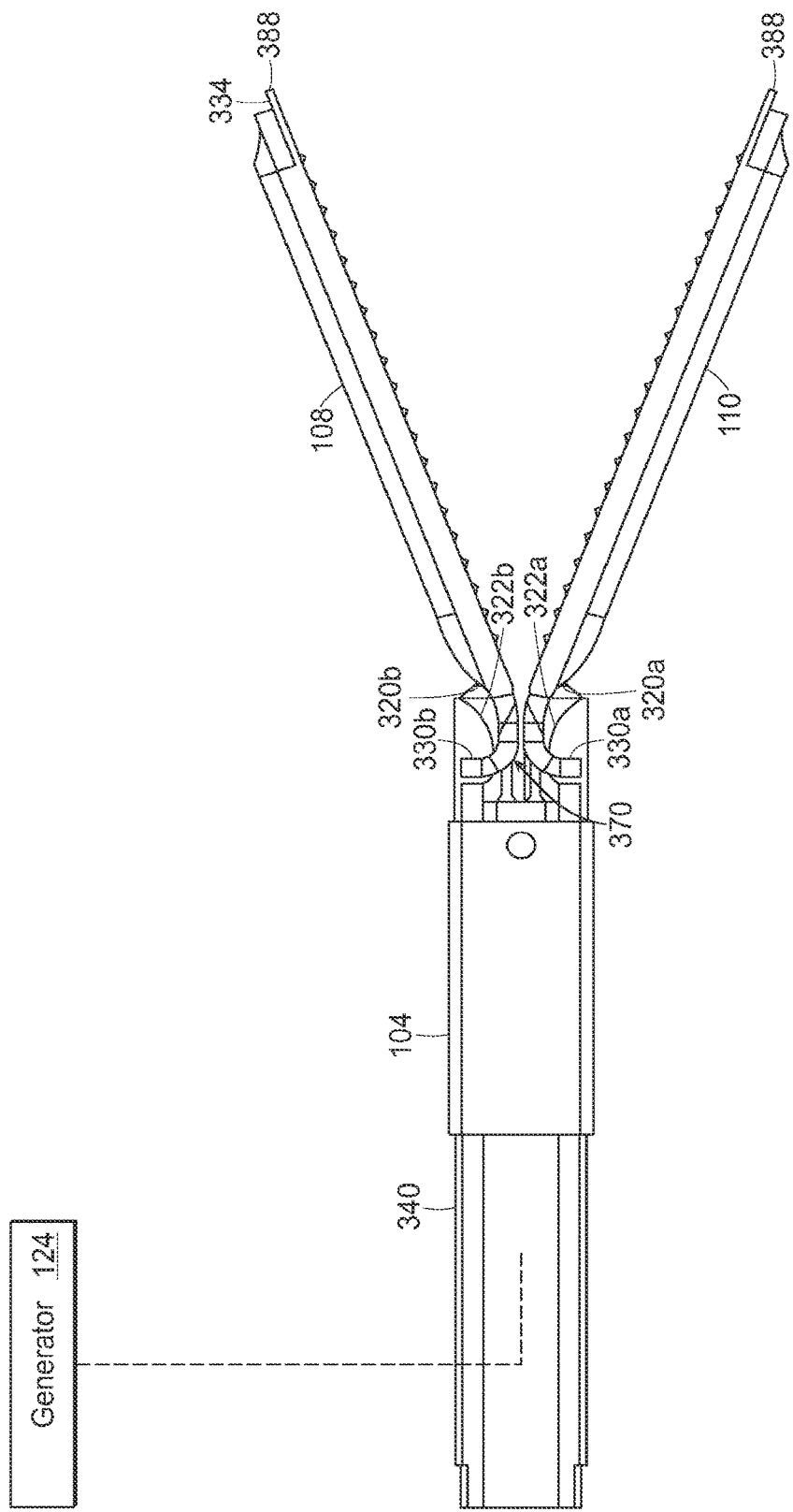
FIGS. 7 and 8 illustrate one embodiment of the actuation of a reciprocating member shown in FIG. 3 from a first retracted position to a second extended position to move the jaws of the end effector from an open position to a closed position.
Figure 8:
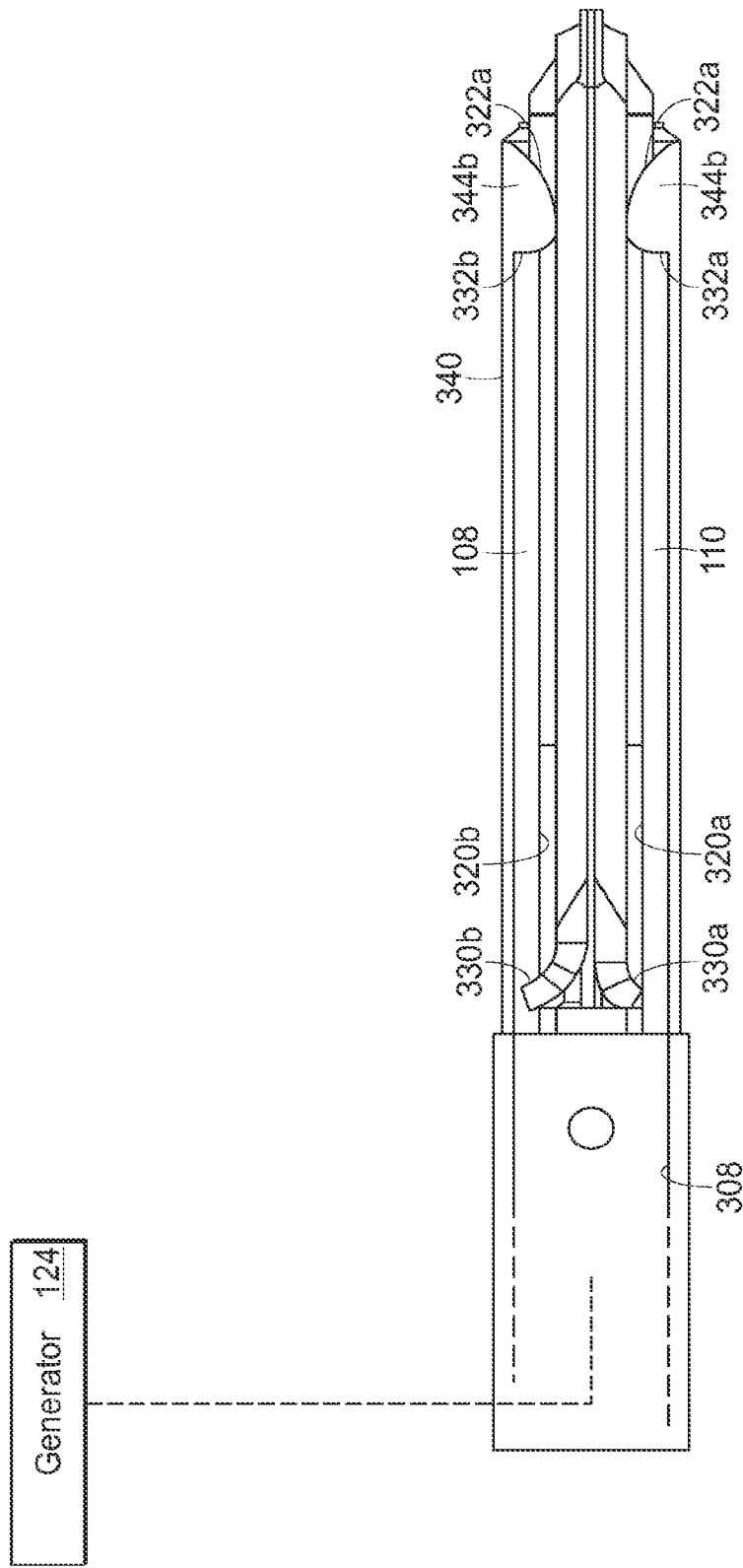

FIGS. 7 and 8 illustrate one embodiment of the actuation of the reciprocating member 340 from a first retracted position to a second extended position to move the jaws 110 and 108 from an open position to a closed position. Referring to FIG. 7, it can be seen that the translatable member 340 is being moved in the proximal direction so that the proximal-facing surfaces 332a and 332b (FIG. 5) of reciprocating member 340 about the outer surfaces 330a and 330b of the jaws thus forcing the jaws apart, for example to apply dissecting forces to tissues or to open jaws 108 and 110 to engage targeted tissues for hemostasis and transection. FIG. 8 shows the reciprocating member 340 after having been fully extended in the distal direction so that the distal-facing surfaces 322a and 322b of reciprocating member 340 have ridden up and over the proximal arcuate surfaces 320a and 320b of the jaws (and medial outer surfaces 360A and 360B) thus forcing the jaws together thereby producing a compressive force between jaws 108 and 110. According to various embodiments, the orientation of surfaces 322a, 322b of the reciprocating member 340 and/or the arcuate surfaces 320a, 320b may be modified to modify the compression rate provided by the reciprocating member 340. For example, the orientation of the 322a, 322b of the reciprocating member 340 and/or the arcuate surfaces 320a, 320b may vary from one embodiment to another, or may vary within a single embodiment in order to cause variable compression rates within a single stroke of the reciprocating member 340.

Figure 11:
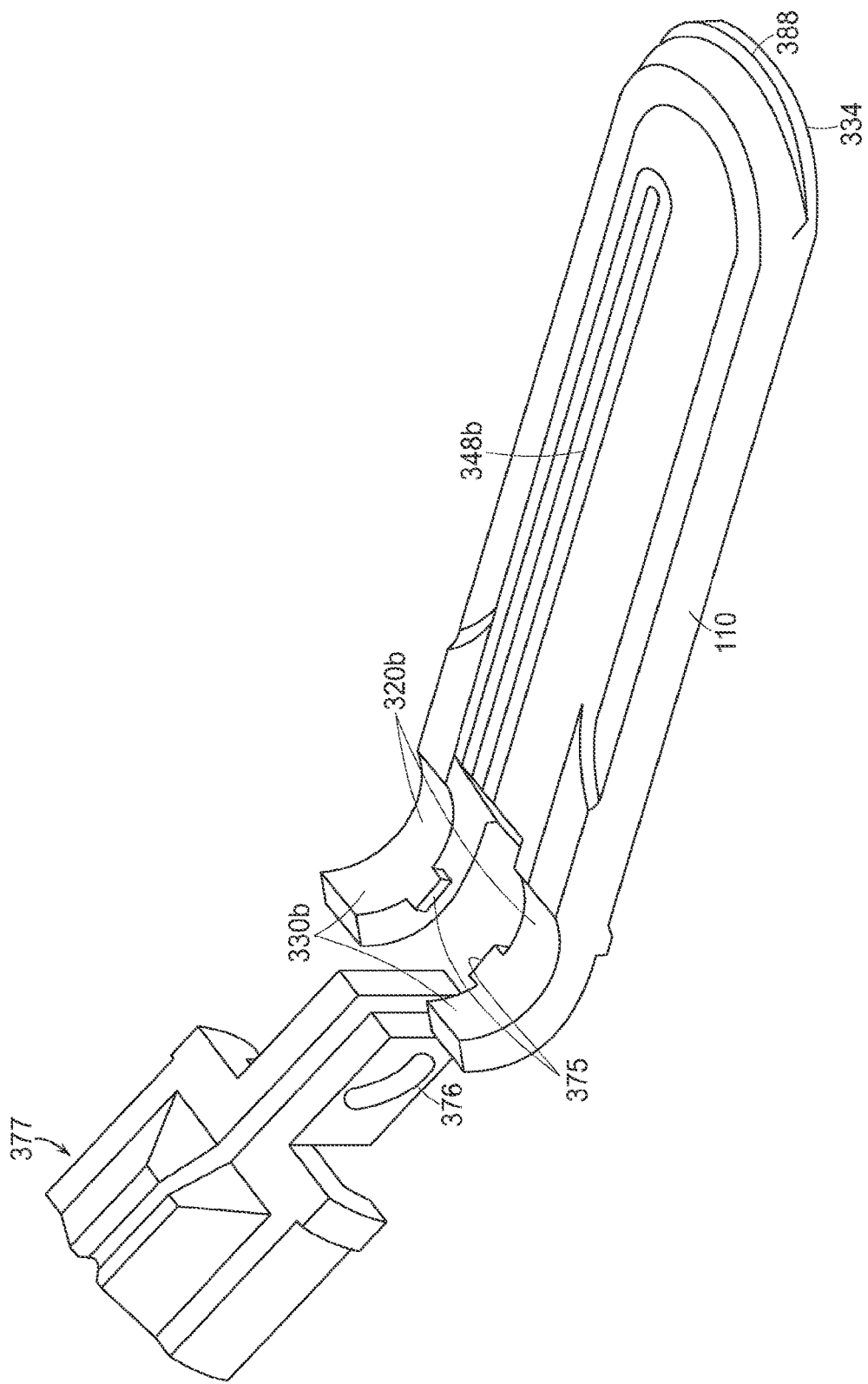
FIG. 11 illustrates one embodiment of the jaw of the end effector of FIG. 3 de-mated from the end effector.

According to various embodiments, the jaws 108, 110 may rollably contact one another along the interface 370 between inner surfaces 372 of the first end 318 of the jaws. As jaws 108 and 110 articulate, the pivot point is moving as the point of contact changes at the interface between surfaces 370 and 372. Thus, the jaw assembly may not need to define a true single pivot point as is typical of hinge-type jaws known in the art. The pivotable action of the jaws along interface 370 may be described as a rolling pivot that optionally can allow for a degree of dynamic adjustment of the engagement gap g at the proximal end of the jaws. FIG. 11 illustrates one embodiment of the jaw 108 de-mated from the end effector 106. Referencing FIG. 11, the jaws elements 110, 108 can be retained relative to one another and the shaft 104 by means of protruding elements 375 that couples with arcuate slots 376 in an internal member 377 that is fixedly carried in bore 308 of shaft 104. Alternatively, outwardly protruding elements can cooperate with slots in the wall of shaft 104. Also, for example, the jaw assembly may (optionally) comprise springs for urging the jaws toward the open position, or closed position depending on the desired at-rest state of the device.

Figure 12:
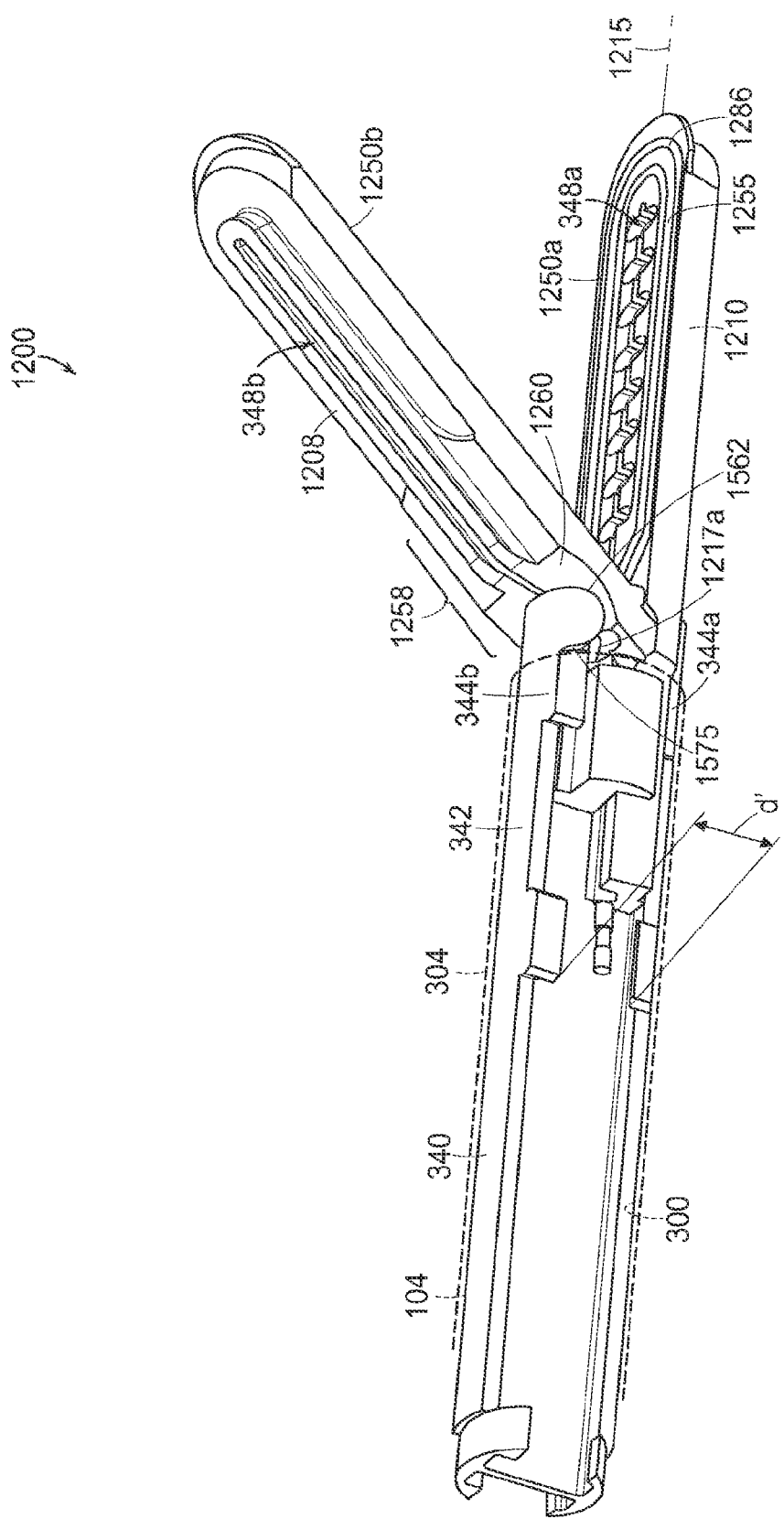
FIGS. 12-14 illustrate one embodiment of an end effector having a single rotating jaw member.
Figure 13:
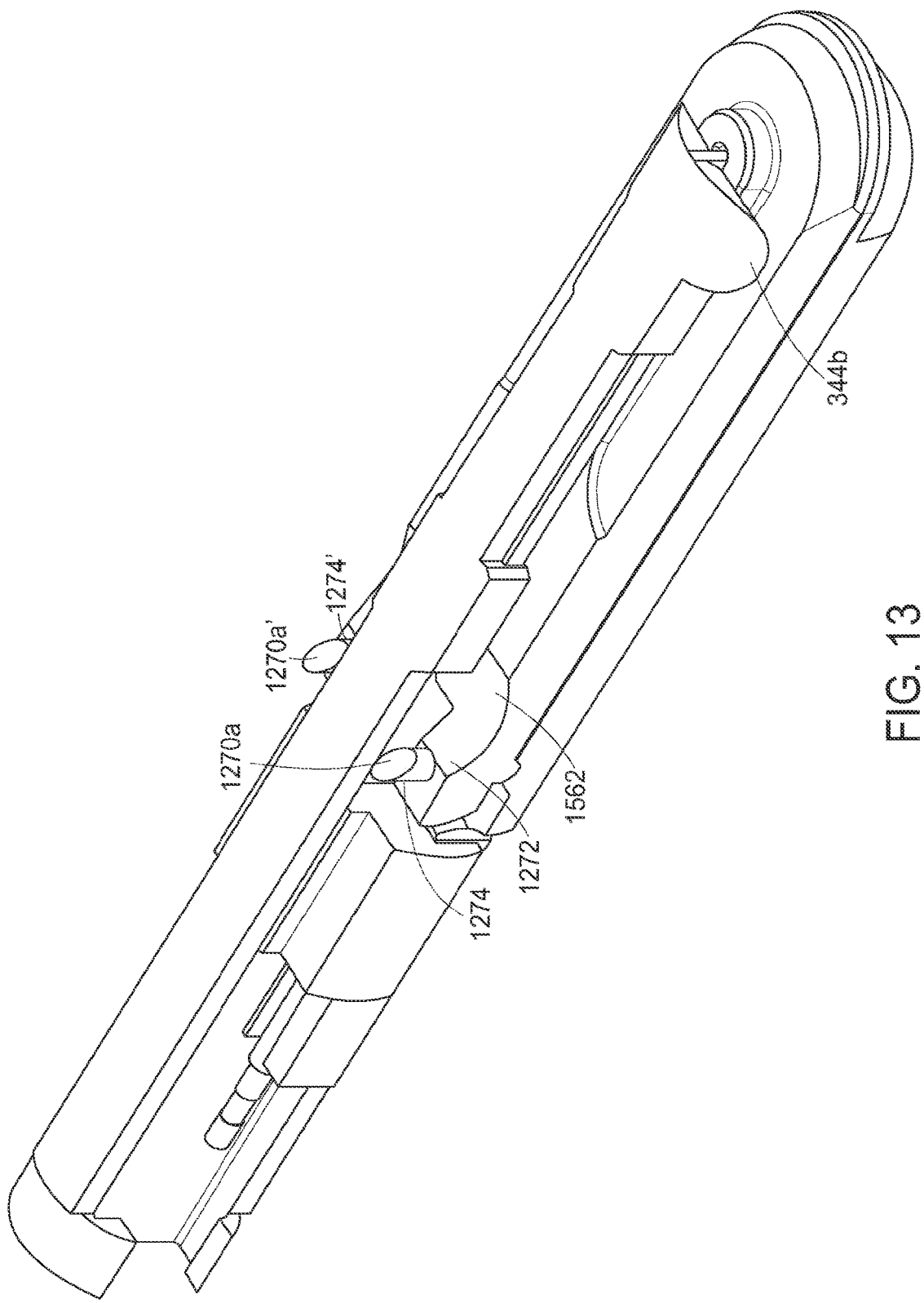

FIGS. 12-13 illustrate an one embodiment of an end effector 1200 having a single rotating jaw member. Like the end effector 106 described above, the end effector 1200 is carried at the distal end 304 of the shaft 104 that has a bore 308 extending therethrough. According to various embodiments, the first (lower) jaw 1210 may be a fixed extension portion of the shaft 104. As can be seen in FIGS. 12 and 13, the second (upper) jaw 1208 is adapted to close or approximate along longitudinal axis 1215.

The opening-closing mechanism of end effector 1200 may provide cam surfaces for positive engagement between reciprocating member 340 and the jaws (i) for moving the jaws to a closed position to engage tissue under high compressive forces, and (ii) for moving the jaws toward the (first) open position thereby providing high opening forces to dissect tissue with outer surfaces of the jaw tips. The reciprocating member 340 operates as described previously to reciprocate within bore 308 of the shaft 104. As can be seen in FIG. 13, the distal end portion 342 of reciprocating member 340 carries distal first and second laterally-extending flange portions 344A and 344B with the blade-carrying transverse element 345 extending therebetween. The blade-carrying member slides within channels 348a and 348b in the jaws.

In the example embodiment of FIGS. 12 and 13, the first and second jaw members 1210 and 1208 again define engagement surfaces or planes 1250*a* and 1250*b* that deliver energy to engaged tissue. The engagement planes may carry one or more conductor/electrodes 1255 and, in various embodiments, may comprise a PTC matrix 1285 in at least one of the jaws' engagement surfaces 1250*a* and 1250*b*. In the embodiment of FIGS. 12 and 13, the upper jaw 1208 has a proximate end region 1258 that, in the open position, defines a first (proximally-facing) arcuate cam surface indicated at 1260 that is engaged by a first surface portion 1562 of the reciprocating member 340. The first (proximal) end region 1258 of the upper jaw, in the open position, further defines second (distally-facing) surface portions indicated at 1270*a* and 1270*a'* that are engaged by second surface 1272 of reciprocating member 340 for moving the jaw assembly to an open position.

Figure 14:
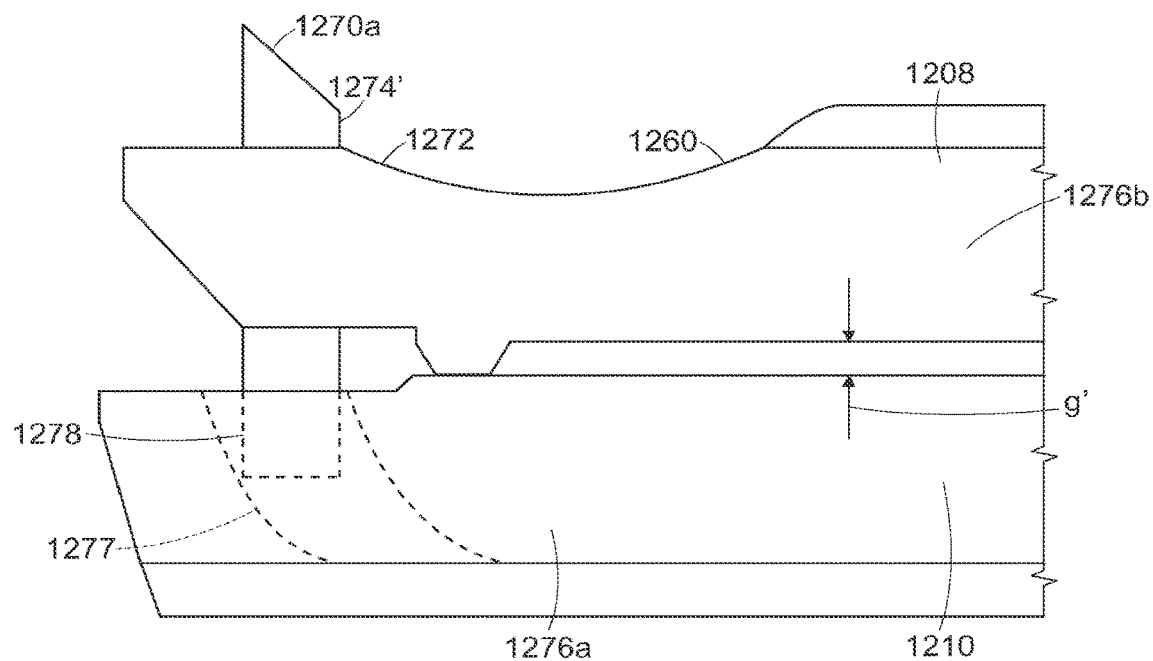

As can be seen best in FIG. 13, the cam surfaces 1270*a* and 1270*a'* may be formed into pins or projecting elements 1274 and 1274' that may serve multiple purposes. Referring to FIG. 14, the pins 1274 and 1274' extend through the upper jaw body 1276*b* and are received within arcuate bores 1277 in body 1276*a* of lower jaw 1210. The lower portions 1278 (collectively) of the pins 1274 and 1274' thus can retain upper jaw 1208 and prevent it from moving axially or laterally relative to the jaw axis 1215 while still allowing the jaw's rotation for opening and closing. The pin mechanism further allows for greatly simplified assembly of the instrument.

Figure 19:
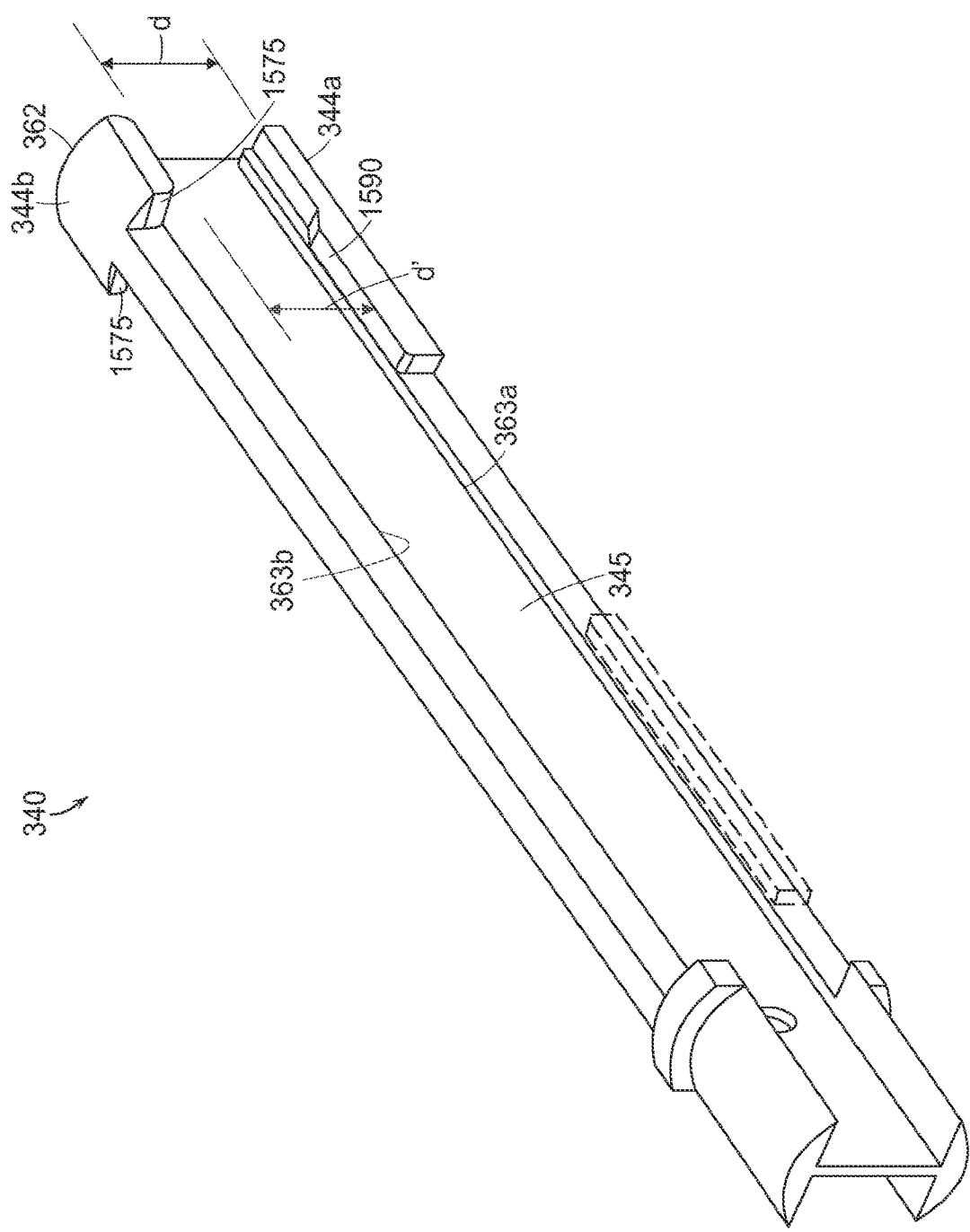
FIG. 19 illustrates one embodiment of the reciprocating member configured with separate elevated step or cam surfaces in the lower flange portions that are adapted to slidably engage the ends of the rectangular pins on either side of upper jaw.

The pins 1274 and 1274' may provide additional functionality by providing a degree of "vertical" freedom of movement within the first (proximal) end portion 1258 of the jaw. As can be seen in FIGS. 12 and 19, the distal laterally-extending flange portions 344A and 344B define a transverse dimension d (cf. FIG. 19) that in turn determines the dimension of the engagement gap g of the distal end of the jaws in the jaw-closed position (FIG. 14). The transverse dimension d equals the dimension between inner surfaces of flange portions 344A and 344B that slidably contact the outer surfaces of both jaws.

Figure 16:
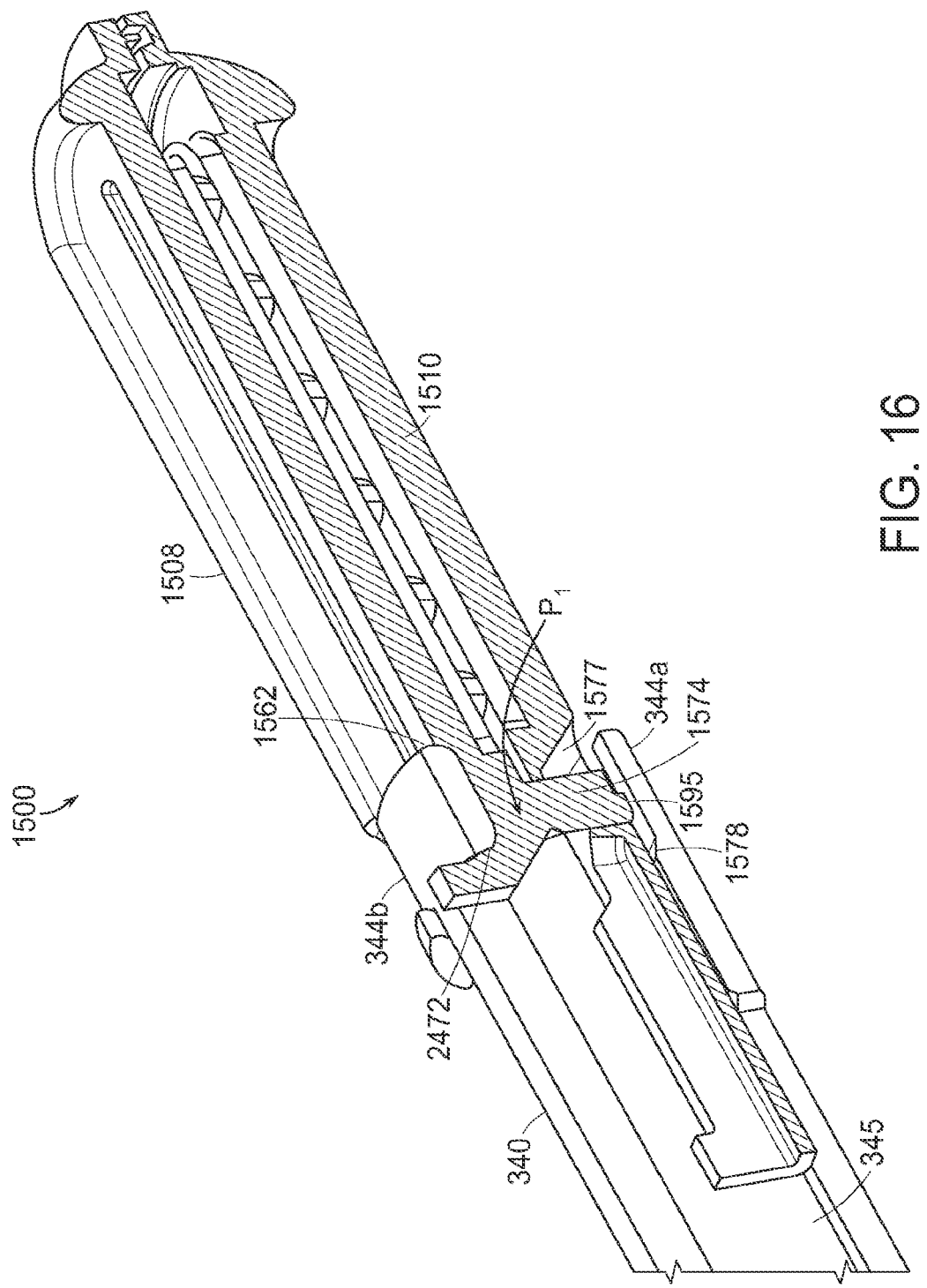
Figure 17:
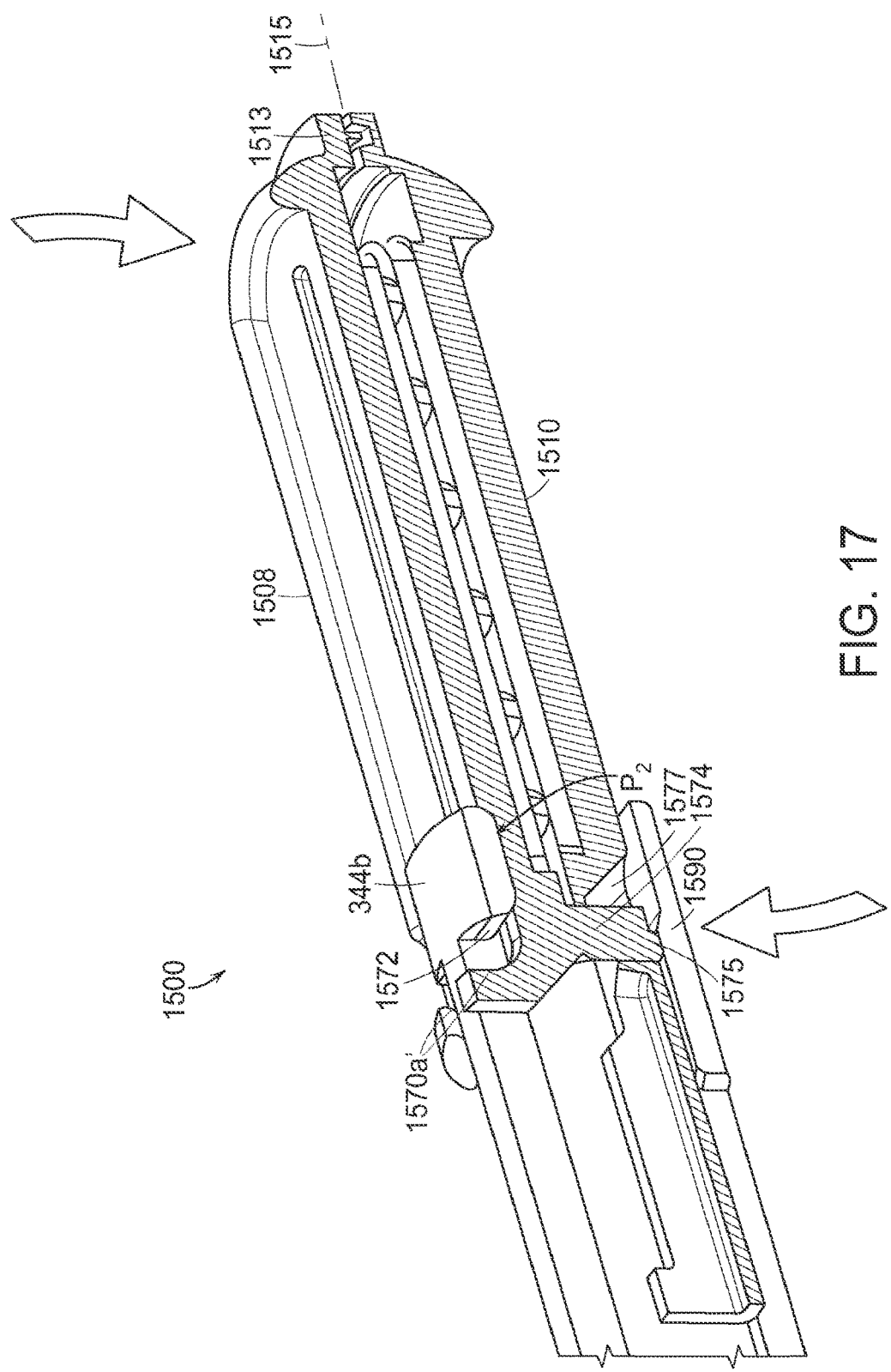
Figure 18:
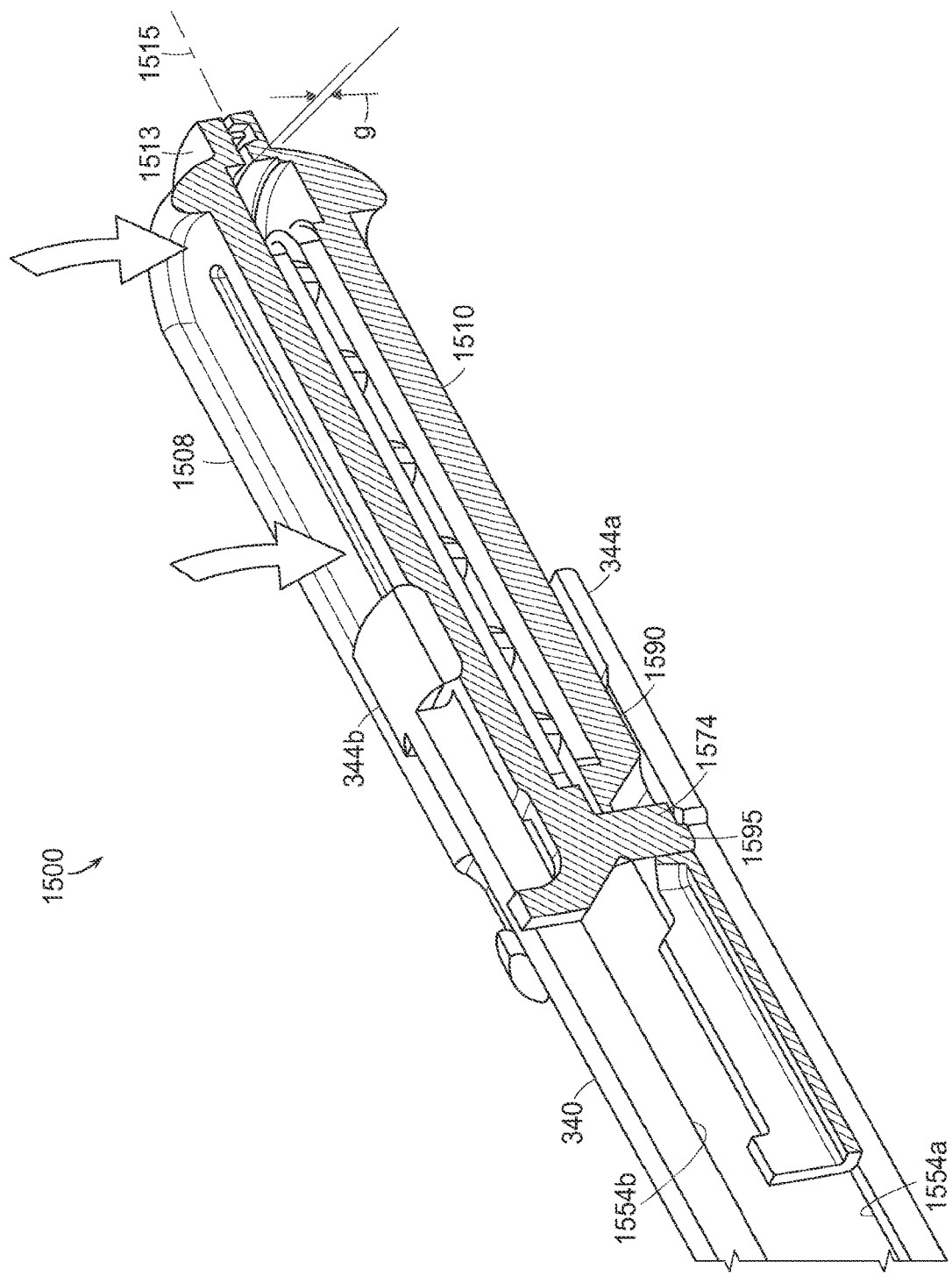

FIGS. 15-18 illustrate another embodiment of an end effector 1500 that provides both electrosurgical functionality and improved grasping and dissecting functionality for endoscopic surgeries. In FIGS. 15-18, both the upper and lower jaws are shown in cut-away views to show internal cam surfaces of the upper jaw 1510 and the reciprocating member 340. The jaw assembly 1500 may carry engagement surfaces for applying electrosurgical energy to tissue as in the previously described embodiments, as well as cutting means for transecting the engaged tissue volume. The jaw assembly 1500 relates to the ability of the jaw structure, in one mode of operation, to be used for general grasping and dissecting purposes wherein the distalmost tips 1513 of the jaws can close tightly on tissue with little movement of the actuator lever 113 in the handle of the instrument. At the same time, in another mode of operation, the jaw assembly 1500 can close to apply very high compressive forces on the tissue to enable welding. Thus, the jaw structure may provide (i) a first non-parallel jaw-closed position for grasping tissue with the distal jaws tips (FIG. 17), and (ii) a second parallel jaw-closed position for high compression of tissue for the application of electrosurgical energy (FIG. 18).

Figure 15:
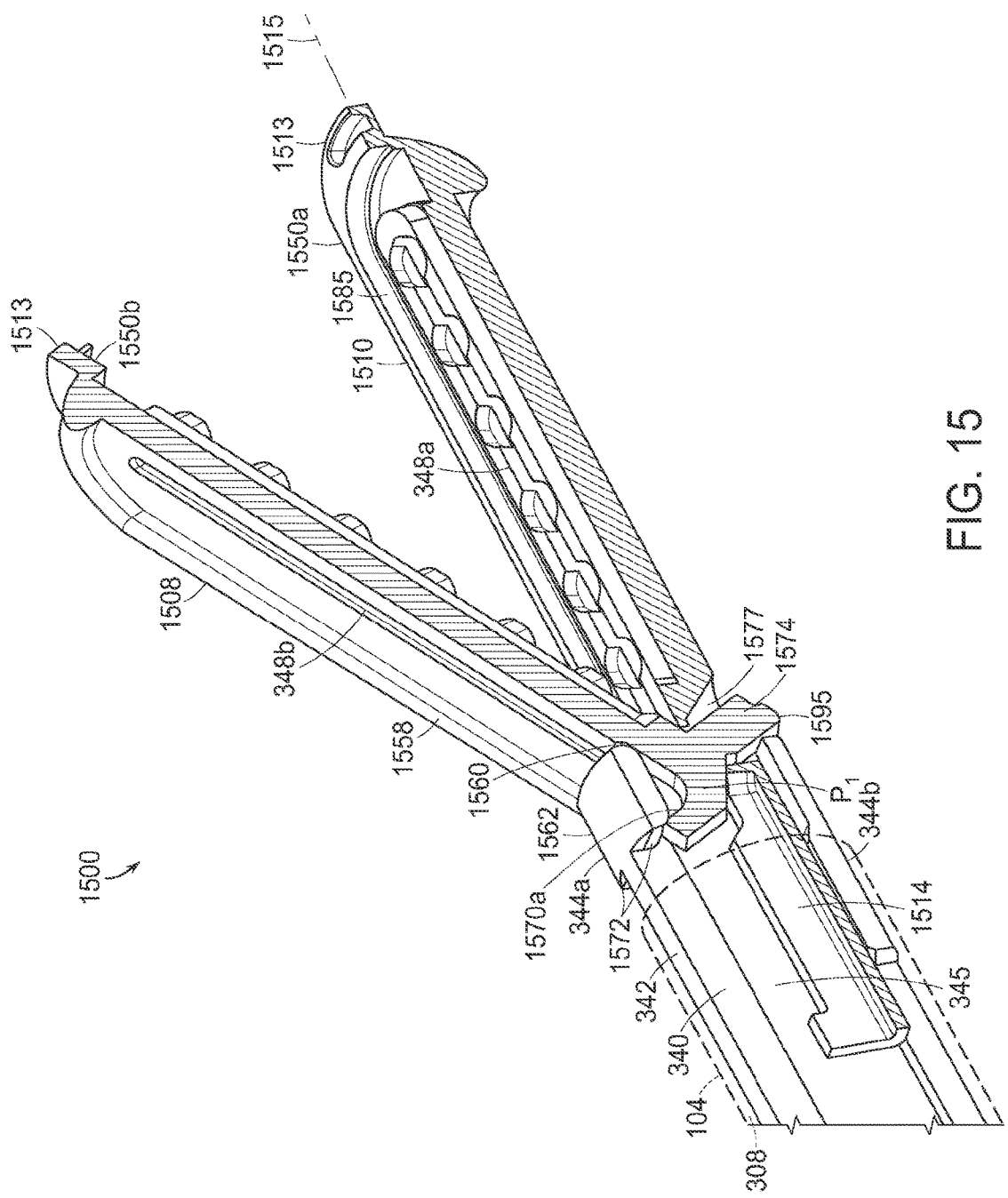
FIGS. 15-18 illustrate another embodiment of an end effector having a single rotating jaw member.

Referring to FIG. 15, the end effector 1500 again has a shaft 104 that is similar to the shaft 104 as used by the end effector 1200 with first (lower) jaw 1510 comprising a fixed extending portion 1514 of the shaft 104. As can be seen in FIG. 15, the second (upper) jaw 1508 is adapted to close or approximate about longitudinal axis 1515. The opening-closing mechanism of jaw assembly 1500 provides cam elements and cooperating jaw surfaces for positive engagement between the reciprocating member 340 as described previously (i) for moving the jaws to a closed position to engage tissue, and (ii) for moving the jaws toward the open position thereby providing high opening forces to dissect tissue with outer surfaces of the jaw tips 313.

The reciprocating member 340 (FIG. 19) operates as described previously to reciprocate within bore 308 of the shaft 104 (FIG. 15). As can be seen in FIG. 15, the distal end 342 of the reciprocating member 340 again carries distal flange portions 344A and 344B with a blade-carrying transverse portion 345 therebetween. The transverse portion 345 slides within channels 348*a* and 348*b* in the paired jaws. In the example embodiment of FIG. 15, the first and second jaws 1510 and 1508 again define engagement surfaces 1550*a* and 1550*b* that can deliver electrosurgical energy to engaged tissue.

In the embodiment of FIG. 15, the upper jaw 1508 has a proximal end 1558 that defines a first (proximally-facing) arcuate jaw surface 1560 that is engaged by a first cam surface element 1562 of reciprocating member 340 for opening the jaw. The proximal end 1558 of the upper jaw further defines second (distally-facing) jaw surface portions indicated at 1570*a* and 1570*a'* that are engaged by second cam element 1572 of reciprocating member 340 for moving the jaw assembly to an open position.

The embodiment of FIG. 15 shows that the upper jaw 1508 has a floating primary pivot location indicated at $P_1$ that is provided by the projecting elements or rectangular pins 1574 (collectively) on either side of the channel portions 348*a* that slidably extend into bores 1577 (collectively) in the lower jaw body (cf. Figure 14). The lower portions of the pins 1574 thus allow upper jaw 1508 to rotate while at the same time the pin-and-bore mechanism allows the upper jaw to move upwardly away from the lower jaw.

For example, the degree of "vertical" freedom of movement of the upper jaw allows for the system to "tilt" the distal tip 1513 of upper jaw 1508 toward the axis 1515 to thereby allow the distal jaw tips 1513 to grasp tissue. This is termed a non-parallel closed position herein. The tilting of the jaw is accomplished by providing a plurality of cam surfaces in the upper jaw 1508 and the reciprocating member 340.

As can be seen in FIGS. 15 and 19, the lower and upper laterally-extending flange portions 344A and 344B of the reciprocating member 340 define a transverse dimension d that determines the dimension of gap g between the engagement surface of the jaws in the fully jaw-closed position (FIG. 18). The transverse dimension d equals the dimension between inner surfaces of flange portions 344A and 344B that slidably contact the outer surfaces of both jaws.

FIG. 19 illustrates one embodiment of the reciprocating member 340 configured with separate elevated step or cam surfaces 1590 in the lower flange portions 344A that are adapted to slidably engage the ends 1595 of the rectangular pins 1574 on either side of upper jaw 1508. The elevated cam surfaces 1590 of reciprocating member 340 thus create another transverse dimension d' between inner surfaces of the flange portions 344A and 344B that move the jaws toward either the first jaw-closed position or the second jaw-closed position.

Now turning to FIGS. 15-18, the sequence of cut-away views illustrate how the multiple cam surfaces cause the jaws to move between a first "tilted" jaw-closed position to a second "high-compression" jaw-closed position. In FIG.

15, the jaws are in an open position. In FIG. 16, the reciprocating member 340 is moved distally and its cam surface element 1562 pushes on jaw surfaces 1560 to move the jaws toward a closed position wherein the jaws rotate about primary pivot location $P_i$. In FIG. 16, it can be seen that the elevated cam surfaces 1590 in the lower flange 344A have not yet engaged the ends 1595 of the rectangular pins 1574.

Now turning to FIG. 17, the reciprocating member 340 is moved further distally wherein the elevated cam surfaces 1590 of lower flange 344A have now engaged and elevated the ends 1595 of rectangular pins 1574 thereby tilting the upper jaw. The upper jaw 1508 is tilted slightly by forces in the direction of the arrows in FIG. 17 as the upper flange 1544B holds the upper jaw 1508 at a secondary pivoting location indicated at $P_2$—at the same time that the step of the cam surface element 1590 lifts the pins 1574 and the proximal portion 1558 of the upper jaw 1508 upward.

Thus, the system functions by providing a slidable cam mechanism for lifting the proximal end of the jaw while maintaining the medial jaw portion in a fixed position to thereby tilt the distal jaw to the second jaw-closed position, with the pivot occurring generally about secondary pivot $P_2$ which is distal from the primary pivot location $P_1$.

FIG. 18 next shows the reciprocating member 340 moved further distally wherein the elevated cam surfaces 1590 of lower flange 344A slides distally beyond the ends 1595 of rectangular pins 1574 thus causing the flanges 344A and 344B together with the trailing edge portions 1575 of the "I"-beam portion (FIG. 19) of the member 340 to apply very high compression forces over the entire length of the jaws as indicated by the arrows in FIG. 18. This position is termed a parallel jaw-closed position herein. Another advantage is that the jaw structure is in a "locked" position when the reciprocating member 340 is fully advanced.

Figure 20:
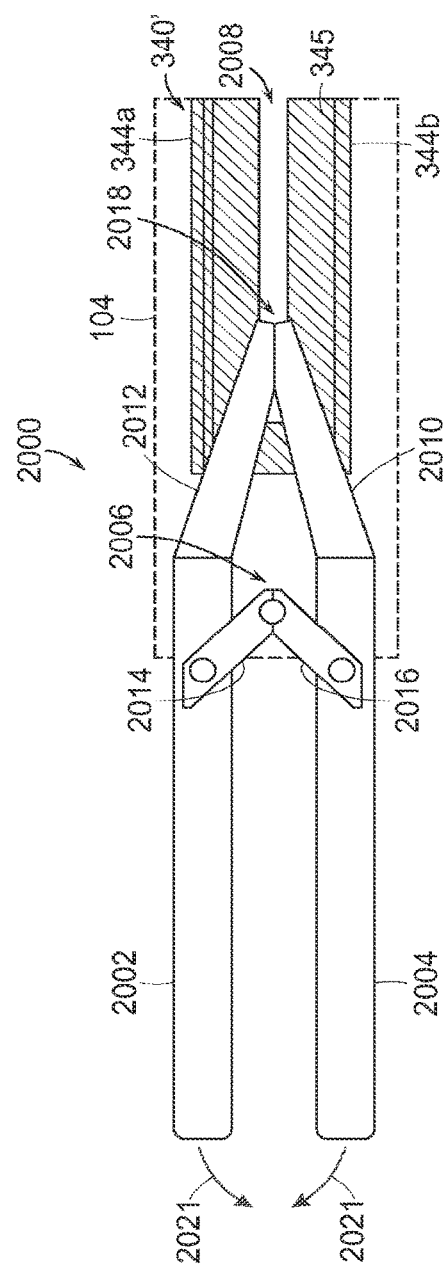
FIG. 20 illustrates one embodiment of an end effector comprising a first jaw member and a second jaw member that are configured to have a parallel closing motion.

FIG. 20 illustrates one embodiment of an end effector 2000 comprising a first jaw member 2002 and a second jaw member 2004 that are configured to have a parallel closing motion via a linkage system. The end effector 2000 may be coupled to the shaft 104, which is shown in FIG. 20 as a transparent outline to illustrate the interior components. The end effector 2000, in addition to the jaw members 2002, 2004, may comprise push rods 2012, 2010 and linkage members 2014, 2016 as well as a reciprocating member 340', which may operate similar to the reciprocating member 340 described above. The push rods 2012, 2010 may be pivotably coupled to the respective jaw members 2002, 2004. The push rods 2012, 2010 may be pivotably coupled to one another at pivot point 2018. Pivot point 2018 may, additionally, be coupled to the shaft 104, for example, to an interior portion of the shaft 104, such that the pivot point 2018 may be substantially restrained from proximal or distal motion. Pivotable linkage members 2014, 2016 may additionally couple the jaw members 2002, 2004. For example, a linkage member 2014 may be pivotably coupled to the jaw member 2002. Another linkage member 2016 may be pivotably coupled to the jaw member 2004. The members 2014, 2016 may be pivotably coupled to one another at pivot point 2006. Like pivot point 2018, the pivot point 2006 may be coupled to the shaft 104 such that it is substantially restrained from proximal or distal motion. It will be appreciated that the various pivot points 2006, 2018 as well as other pivotable joints (e.g., between jaw members 2002, 2004 and the various push rods 2010, 2012 and linkage members 2014, 2016) may be implemented by pivot pins or any other suitable pivotable fastening device or method (hinges, etc.). According to various embodiments, the reciprocating member 340' may define a slot 2008. The pivot point 2018 (e.g., the pivotably fastening device implementing the pivot point 2018) may extend through the slot 2008. Accordingly, the reciprocating member 340' may translate distally and proximally without causing any related distal or proximal movement of the pivot point 2018.

Figure 21:
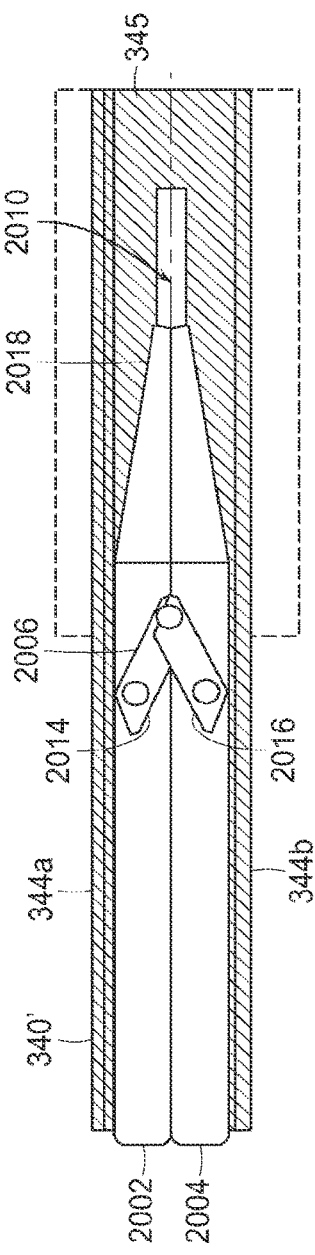
FIG. 21 illustrates one embodiment of the end effector of FIG. 20 in a closed position.

In FIG. 20, the end effector 2000 is shown in an open position. FIG. 21 illustrates the end effector 2000 in a closed position. To transition the end effector 2000 from the open position shown in FIG. 20 to the closed position shown in FIG. 21, the clinician may cause the reciprocating member 340' to translate distally (e.g., by using the actuator 113 of FIG. 1). As the reciprocating member 340' translates distally, a transverse element 345 of the reciprocating member 340' may pass through slots in the jaw members 2002, 2004, such as the slot 2022 of jaw member 2002 illustrated in FIG. 22. Flanges or shoulder elements 344A, 344B of the reciprocating member 340' may ride outside of all or a portion of the jaw members 2002, 2004, generating a compressive force tending to close the members 2002, 2004. The compressive force may cause the push rod members 2010, 2012 and the linkage members 2014, 2016 to pivot towards one another about the respective pivot points 2018, 2006 to the position shown in FIG. 21. The jaw members 2002, 2004 may close in a substantially parallel motion. When the position of the pivot points 2018, 2006 is fixed, the jaw members 2002, 2004 may translate slightly distally as they close. This effect is illustrated in FIGS. 20 and 21 and indicated in FIG. 20 by arrows 2021. To transition the jaw members 2002, 2004 from the closed position shown in FIG. 21 to the open position shown in FIG. 20, the reciprocating member 340' may be retracted to remove the compressive force. According to various embodiments, the jaw members 2002, 2004 may then be spring-loaded to return to the open position shown in FIG. 20.

FIG. 22 illustrates a top view of one embodiment of the end effector 2000. In the view illustrated, optional complimentary push rod members 2010', 2012', linkage members 2016', 2014' and pivot points 2006, 2006', 2018, 2018' are illustrated on the opposite side of the end effector 2000. These push rod members 2010', 2012' and linkage members 2014', 2016' may behave in a manner similar to that of the push rod members 2010, 2012 and linkage members 2014, 2016 described above. As illustrated in FIG. 22, the push rod members 2010, 2012, 2010', 2012' may be positioned outside of the jaw members 2002, 2004 (e.g., between the jaw members 2002, 2004 and an interior wall 104a of the shaft 104). Also, as illustrated in FIG. 22, each pair of members may be positioned adjacent one another. For example, push rod members 2010, 2012 are illustrated adjacent to one another, as our push rod members 2010', 2012' and linkage member pairs 2014, 2016 and 2014', 2016'. For example, one of the push rod members 2010, 2012 may be positioned outside of the other push rod member 2010, 2012. It will be appreciated that, according to various embodiments, complimentary pivot points (e.g., 2006, 2006' and 2018, 2018') may be implemented by a single pivot pin or other pivotable fastening device extending through the shaft 104. Regarding complimentary pivot points 2018, 2018', when both are implemented with a single pivot pin or other pivotable fastening device, such device may pass through the slot 2008 of the reciprocating member 340' as described above.

FIG. 23 illustrates a top view of the end effector 2000 of FIG. 22 according to an alternate arrangement 2000'. In FIG. 23, push rod members 2012 and 2012' are illustrated coupled to a proximal end of the visible jaw member 2002'. Push rod members 2010 and 2010' may be positioned below the push rod members 2012, 2012' from the view shown in FIG. 23. In this way, the jaw member 2002' may be wider than the jaw member 2002, for a given diameter of the shaft 104.

FIGS. 24 and 25 illustrate one embodiment of an end effector 2000" mounted to the shaft 104 via a clevis 2400. The end effector 2000" may function in a manner similar to the end effectors 2000 and 2000" described above. Instead of being positioned relative to the shaft 104 such that both pivot points 2006, 2018 are within the shaft 104 proper, the end effector 2000" may comprise a clevis 2400 coupled to the shaft 104. The clevis 2400 may extend from the shaft to the pivot point 2006, which may be coupled to the clevis 2400 such that distal and proximal motion of the pivot point 2006 is substantially arrested. For example, the clevis 2400 may comprise a pair of arms extending from the shaft 104 to receive the pivot pin or other pivotable fastening device implementing the pivot point 2006. The clevis 2400 may be shaped such that the jaw members 2002, 2004 may fit through, allowing the jaw members 2002, 2004 to open wider than the diameter of the shaft 104.

FIGS. 26 and 27 illustrate one embodiment of an end effector 2700 having a single movable jaw member 2702. A second jaw member 2704 may be stationary (e.g., fixed to the shaft 104). A push rod 2708 and linkage 2706 may couple the movable jaw member 2702 to either the shaft 104 or the stationary jaw member 2704. The end effector 2700 may operate in a manner similar to the end effectors 2000, 2000', and 2000" described above. For example, to transition the end effector 2700 from the open position shown in FIG. 26 to the closed position shown in FIG. 27, the reciprocating member 340' may be extended distally. Flange portions 344A, 344B of may contact the jaw members 2702, 2704 in a manner similar to that described above, exerting a compressive force on the jaw members 2702, 2704. This may cause the movable jaw member 2702 to pivot about pivot points 2712, 2714 and in the direction of the arrow 2716 towards the stationary jaw member 2704 to the closed position shown in FIG. 27. It will be appreciated that the push rod 2708 and the linkage 2706 may be positioned in any suitable manner. For example, the push rod 2708 may be positioned between the jaw members 2702, 2704 and an inner wall of the shaft 104, or may be positioned substantially proximal from the jaw members 2702, 2704.

According to various embodiments, the end effectors 106, 1200, 1500, 2000, 2000', 2000", 2700 may be used to cut and fasten tissue utilizing electrical energy. The examples described below are illustrated with the end effector 106. It will be appreciated, however, that similar configurations and techniques may be used with any of the end effectors described above. Referring to the end effector 106 shown in FIGS. 3-4 and 7-8, the electrodes 120, 122 of the end effector 106 may be arranged in any suitable configuration. In use, for example, tissue (not shown) may be captured between the jaw members 108, 110. RF current may flow across the captured tissue between the opposing polarity electrodes 120, 122. This may serve to join the tissue by coagulation, welding, etc. The RF current may be activated according to any suitable control method. For example, according to various embodiments, the electrodes 120, 122 may be used to implement a "power adjustment" approach, a "current-path directing" approach or an approach referred to herein as a "weld" or "fusion" approach. These various approaches are illustrated herein with reference to FIGS. 28-31, which show the walls of an example blood vessel acted upon by various RF end effectors including those using the power adjustment and current-path directing approaches from above.

Figure 28:
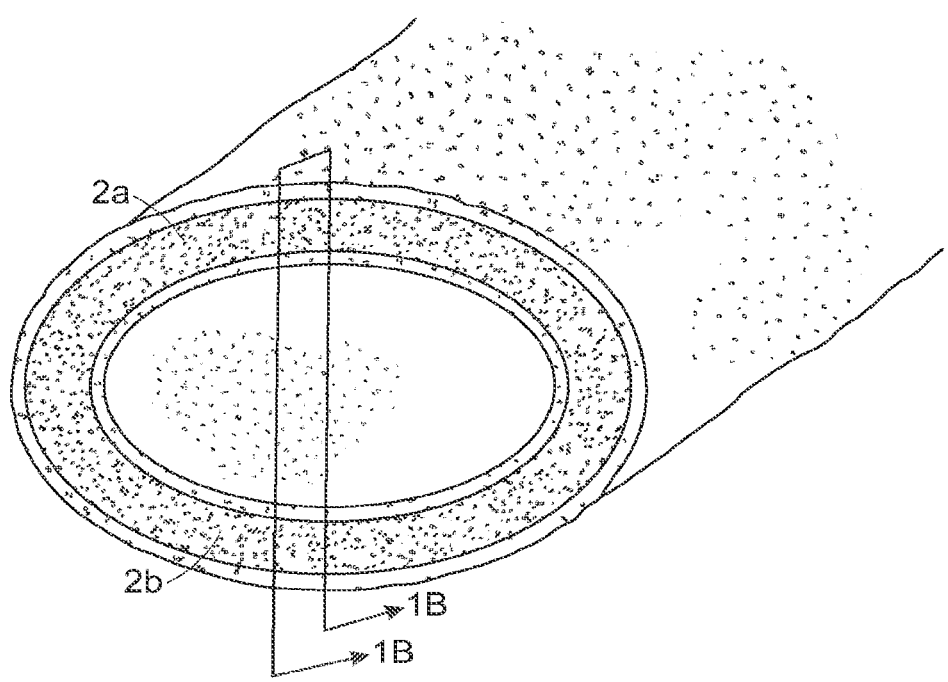
FIG. 28 shows an example embodiment of a vessel having opposing wall portions.
Figure 29:
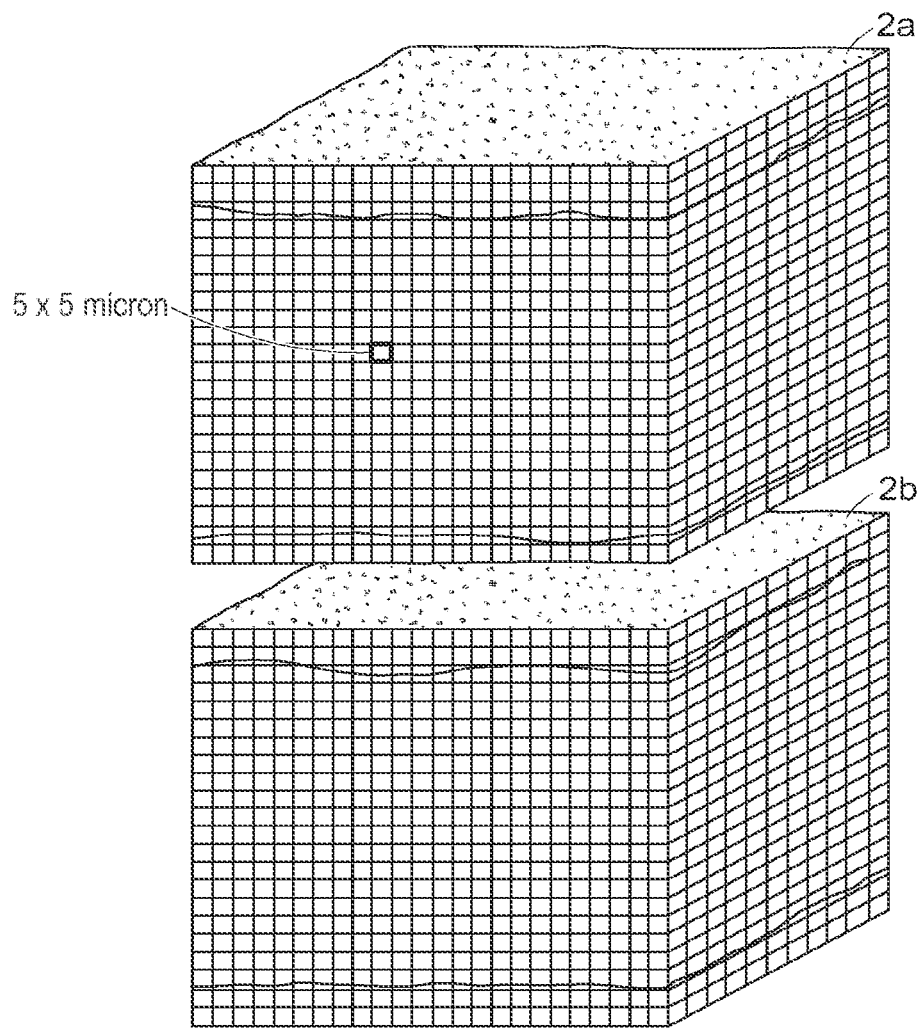
FIG. 29 is a graphic illustration of one embodiment of the opposing vessel walls portions of FIG. 28 with the tissue divided into a grid with arbitrary micron dimensions.

FIG. 28 shows an example embodiment of a vessel having opposing wall portions 2a and 2b. FIG. 29 is a graphic illustration of one embodiment of the opposing vessel walls portions 2a and 2b with the tissue divided into a grid with arbitrary micron dimensions. For example, the grid may represent 5 microns on each side of the targeted tissue. In order to coagulate or weld tissue, collagen and other protein molecules within an engaged tissue volume may be denatured by breaking the inter- and intra-molecular hydrogen bonds. When heat or other energy is removed (e.g., thermal relaxation), the molecules are re-crosslinked to create a fused-together tissue mass. It is desirable that each micron-dimensioned volume of tissue be elevated to the temperature needed to denature the proteins therein in a substantially uniform manner.

Failing to heat tissue portions in a uniform manner can lead to ohmic heating, which can create portions of tissue that are not effectively joined and reduce the strength of the joint. Non-uniformly denatured tissue volume may still be "coagulated" and can prevent blood flow in small vasculature that contains little pressure. However, such non-uniformly denatured tissue may not create a seal with significant strength, for example in 2 mm to 10 mm arteries that contain high pressures. It is often difficult to achieve substantially uniform heating with a bipolar RF device in tissue, whether the tissue is thin or thick. For example, as RF energy density in tissue increases, the tissue surface tends to become desiccated and resistant to additional ohmic heating. Localized tissue desiccation and charring can sometimes occur almost instantly as tissue impedance rises, which then can result in a non-uniform seal in the tissue. Also, many RF jaws cause further undesirable effects by propagating RF density laterally from the engaged tissue thus causing unwanted collateral thermal damage.

Figure 30:
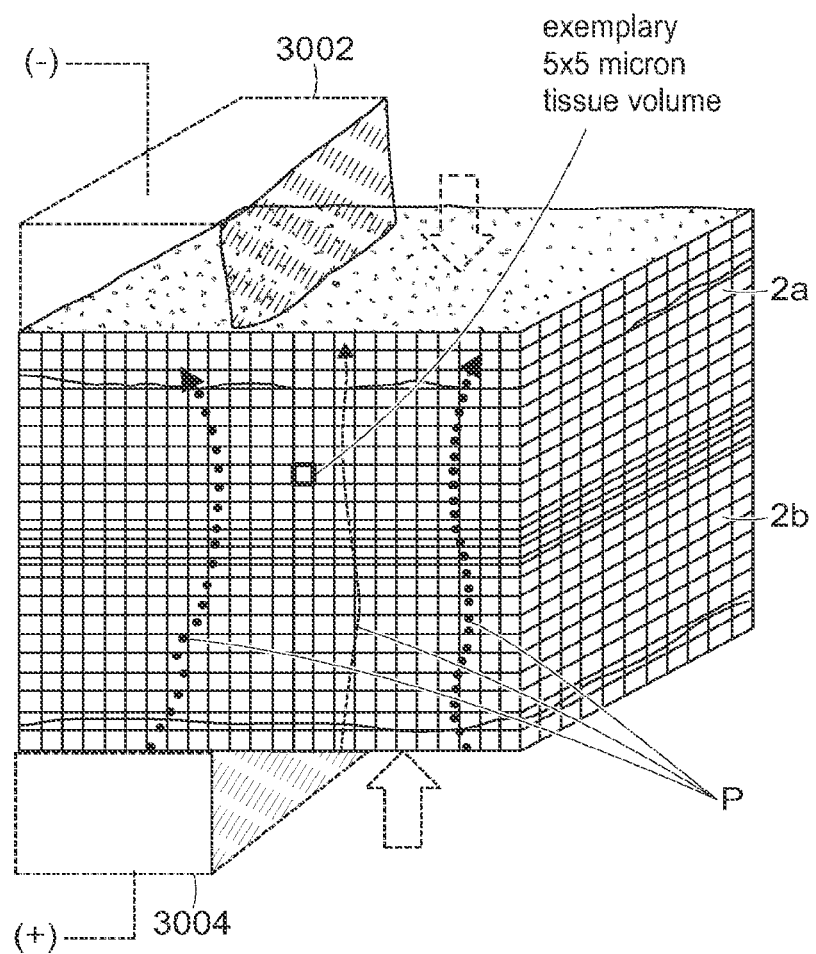
FIG. 30 illustrates one embodiment of the blood vessel of FIG. 28 acted upon by a device implementing a power adjustment approach to energy delivery.

To achieve substantially uniform coagulation, various embodiments described herein may utilize a "power adjustment" approach, a "current-path directing" approach and/or an approach referred to herein as a "weld" or "fusion" approach. According to the "power adjustment" approach, the RF generator 124 can rapidly adjust the level of total power delivered to the jaws' engagement surfaces in response to feedback circuitry, which may be present within the generator 124 and/or at the end effector 106, and may be electrically coupled to the active electrodes. The feedback circuitry may measure tissue impedance or electrode temperature. For example, temperature probes present on the jaw members 109, 110, 1202, 1204 may be in communication with the generator 123 and may sense electrode temperature. FIG. 30 illustrates one embodiment of the blood vessel of FIG. 28 acted upon by a device implementing a "power adjustment" approach to energy delivery. Opposing vessel walls 2a and 2b are shown compressed with cut-away phantom views of opposing polarity electrodes 3002, 3004 on either side of the tissue. For example, the electrode 3002 may be positioned on one jaw member 108, 110, while the electrode 3004 may be positioned on the opposite jaw member. One advantage of such an electrode arrangement is that 100% of each jaw engagement surface comprises an "active" conductor of electrical current—thus no tissue is engaged by an insulator which theoretically would cause a dead spot (no ohmic heating) proximate to the insulator.

FIG. 30 also graphically depicts current paths p in the tissue at an arbitrary time interval that can be microseconds (μs) apart. Such current paths p would be random and constantly in flux—along transient most conductive pathways through the tissue between the opposing polarity electrodes. The thickness of the paths is intended to represent the constantly adjusting power levels. Typically, the duration of energy density along any current path p is on the order of microseconds and the thermal relaxation time of tissue is on the order of milliseconds. Instruments using the power adjustment approach may be useful for sealing relatively small vessels with relatively low fluid pressure. This is because, given the spatial distribution of the current paths and the dynamic adjustment of their power levels, it is unlikely that enough random current paths will revisit and maintain each discrete micron-scale tissue volume at the targeted temperature before thermal relaxation. Also, because the hydration of tissue is constantly reduced during ohmic heating—any region of more desiccated tissue will lose its ohmic heating, rendering it unable to be "welded" to adjacent tissue volumes.

In a second "current-path directing" approach, the end effector jaws carry an electrode arrangement in which opposing polarity electrodes are spaced apart by an insulator material, which may cause current to flow within an extended path through captured tissue rather than simply between surfaces of the first and second jaws. For example, electrode configurations similar to those shown below in FIG. 31 may be implemented on tissue engaging surfaces 350a, 350b, 1236a, 1236b.

Figure 31:
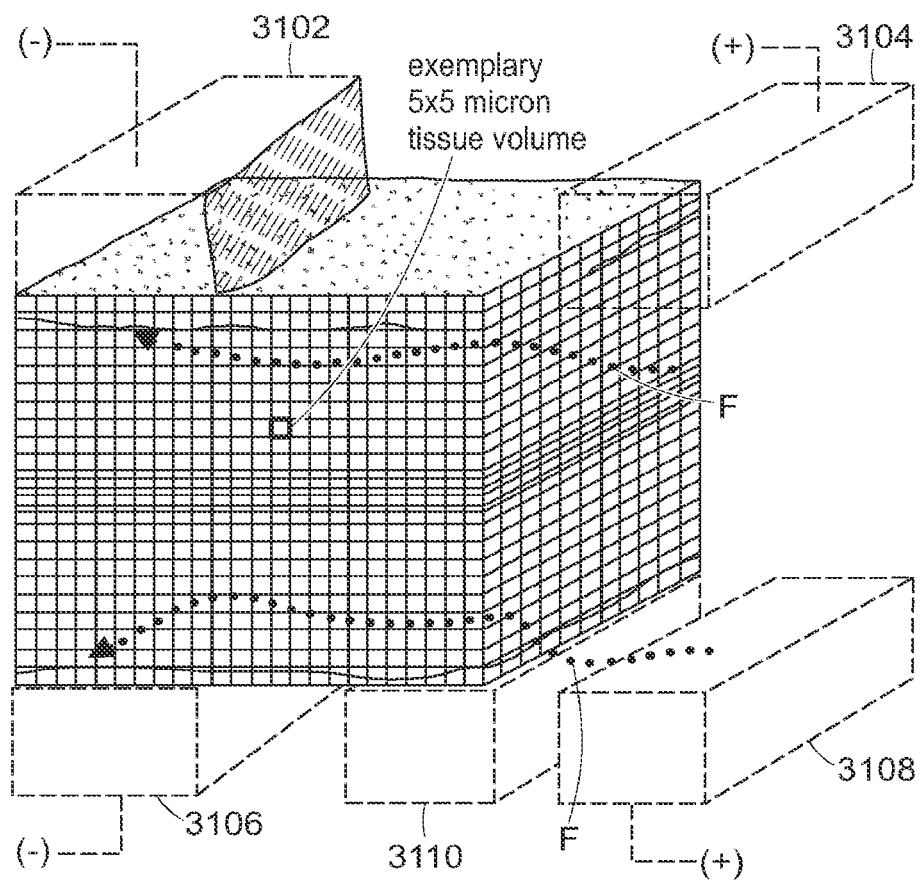
FIG. 31 illustrates one embodiment of the blood vessel of FIG. 28 acted upon by a device implementing a current-path directing approach to energy delivery.

"Current-path directing" techniques are also used to improve the quality of energy-delivered seals. FIG. 31 illustrates one embodiment of the blood vessel of FIG. 28 acted upon by a device implementing a current-path directing approach to energy delivery. In FIG. 31, vessel walls 2a and 2b are engaged between opposing jaws surfaces with cut-away phantom views of electrodes 3102, 3104, 3106, 3108, with opposing polarity (+) and (−) electrodes (3102, 3104 and 3106, 3108) on each side of the engaged tissue. For example, electrodes 3102 and 3104 may be positioned on one of the jaw members 108, 110, 1202, 1204 while electrodes 3106 and 3108 maybe positioned on the opposite jaw member. An insulator 3110 is shown in cut-away view that electrically isolates the electrodes in the jaw. The tissue that directly contacts the insulator 3110 will only be ohmically heated when a current path p extends through the tissue between the spaced apart electrodes. FIG. 31 graphically depicts current paths p at any arbitrary time interval, for example in the µs range. Again, such current paths p will be random and in constant flux along transient conductive pathways.

A third approach, according to various embodiments, may be referred to as a "weld" or "fusion" approach. The alternative terms of tissue "welding" and tissue "fusion" are used interchangeably herein to describe thermal treatments of a targeted tissue volume that result in a substantially uniform fused-together tissue mass, for example in welding blood vessels that exhibit substantial burst strength immediately post-treatment. Such welds may be used in various surgical applications including, for example, (i) permanently sealing blood vessels in vessel transection procedures; (ii) welding organ margins in resection procedures; (iii) welding other anatomic ducts or lumens where permanent closure is desired; and also (iv) for performing vessel anastomosis, vessel closure or other procedures that join together anatomic structures or portions thereof.

The welding or fusion of tissue as disclosed herein may be distinguished from "coagulation", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the treated tissue.

A "weld," for example, may result from the thermally-induced denaturation of collagen and other protein molecules in a targeted tissue volume to create a transient liquid or gel-like proteinaceous amalgam. A selected energy density may be provided in the targeted tissue to cause hydrothermal breakdown of intra- and intermolecular hydrogen crosslinks in collagen and other proteins. The denatured amalgam is maintained at a selected level of hydration—without desiccation—for a selected time interval, which may be very brief. The targeted tissue volume may be maintained under a selected very high level of mechanical compression to insure that the unwound strands of the denatured proteins are in close proximity to allow their intertwining and entanglement. Upon thermal relaxation, the intermixed amalgam results in protein entanglement as re-crosslinking or renaturation occurs to thereby cause a uniform fused-together mass.

To implement the welding described above, the electrodes 120, 122 (or electrodes that are part of the other end effector embodiments described herein) may, one or both, comprise an electrically conductive portion, such as copper or another suitable metal or alloy, and a portion comprising a positive temperature coefficient (PTC) material having a selected increased resistance that differs at selected increased temperatures thereof. The PTC material may be positioned between the electrically conductive portion and any tissue to be acted upon by the end effector 106. One type of PTC material is a ceramic that can be engineered to exhibit a selected positively slope curve of temperature-resistance over a temperature range of about 37° C. to 100° C. Another type of PCT material may comprise a polymer having similar properties. The region at the higher end of such a temperature range brackets a targeted "thermal treatment range" at which tissue can be effectively welded. The selected resistance of the PTC matrix at the upper end of the temperature range may substantially terminate current flow therethrough.

In operation, it can be understood that the electrodes 120 or 122 will apply active RF energy (ohmic heating within) to the engaged tissue until the point in time that the PTC matrix is heated to exceed the maximum of the thermal treatment range. Thereafter, RF current flow from the engagement surface will be lessened—depending on the relative surface areas of the first and second electrodes 120, 122. This instant and automatic reduction of RF energy application may prevent any substantial dehydration of tissue proximate to the engagement plane. By thus maintaining an optimal level of moisture around the engagement plane, the working end can more effectively apply energy to the tissue—and provide a weld thicker tissues with limited collateral thermal effects.

Figure 32:
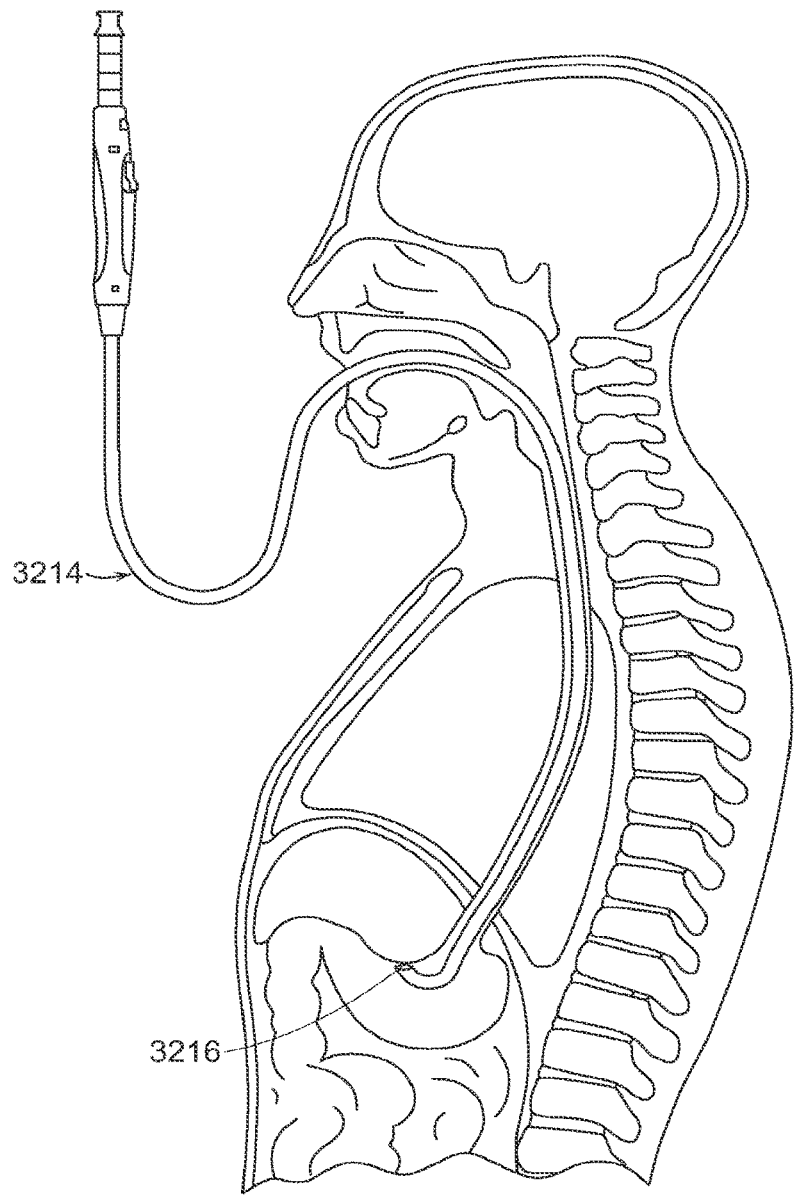
FIG. 32 illustrates one embodiment of an endoscope (illustrated here as a gastroscope) inserted into the upper gastrointestinal tract of a patient.

In various embodiments, surgical instruments utilizing various embodiments of the transection and sealing instrument 100, with the various end effectors and actuating mechanisms described herein may be employed in conjunction with a flexible endoscope. FIG. 32 illustrates one embodiment of an endoscope 3214 (illustrated here as a gastroscope) inserted into the upper gastrointestinal tract of a patient. The endoscope 3214 may be any suitable endoscope including, for example, the GIF-100 model available from Olympus Corporation. The endoscope 3214 has a distal end 3216 that may include various optical channels, illumination channels, and working channels. According to various embodiments, the endoscope 3214 may be a flexible endoscope.

Figure 33:
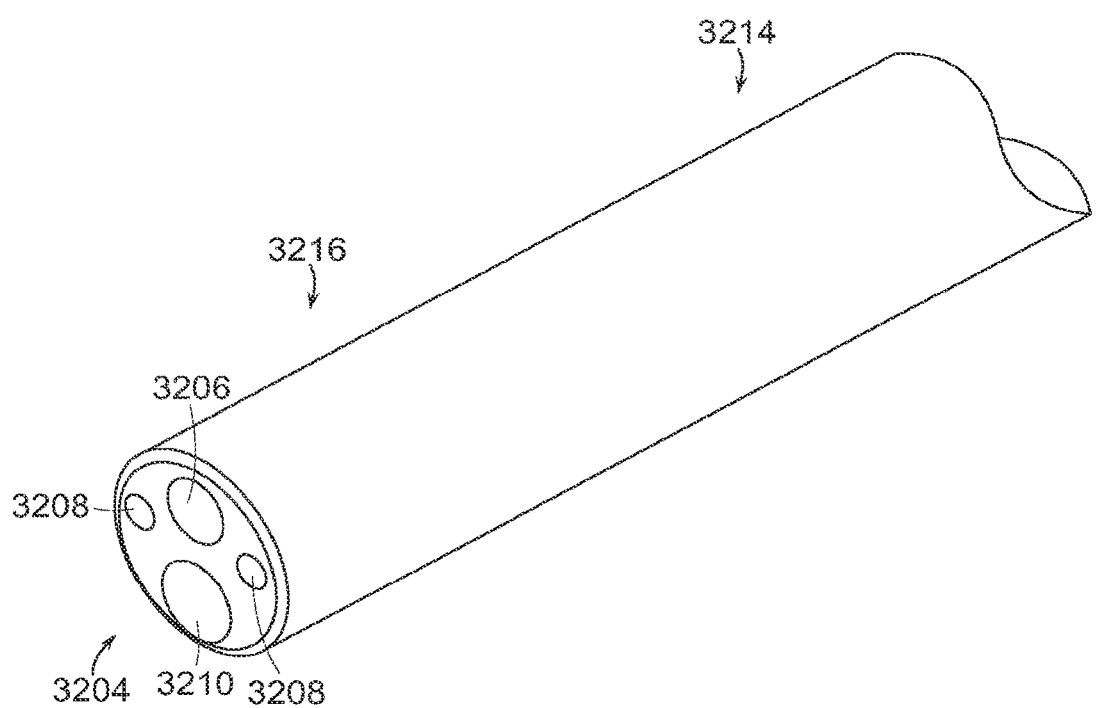
FIG. 33 illustrates one embodiment of a distal portion of the endoscope of FIG. 32, which may be used with the transection and sealing instrument described herein.

FIG. 33 illustrates one embodiment of a distal portion 3216 of the endoscope 3214, which may be used with the transection and sealing instrument 100 described herein. The example endoscope 3214 shown comprises a distal face 3204, which defines the distal ends of illumination channels 3208, an optical channel 3206 and a working channel 3210. The illumination channels 3208 may comprise one or more optical fibers or other suitable waveguides for directing light from a proximally positioned light source (not shown) to the surgical site. The optical channel 3206 may comprise one or more optical fibers or other suitable waveguides for receiving and transmitting an image of the surgical site proximally to a position where the image may be viewed by the clinician operating the endoscope 3214. As described above, the working channel 3210 may allow the clinician to introduce one or more surgical tools to the surgical site. Examples of such surgical tools include scissors, cautery knives, suturing devices, and dissectors. It will be appreciated that the endoscope 3214 is but one example of an endoscope that may be used in accordance with various embodiments. Endoscopes having alternate configurations of optical channels 3206, illumination channels 3208 and/or working channels 3210 may also be used. According to various embodiments, the endoscope 3214 may be, or may be used in conjunction with, steerable devices such as traditional flexible endoscopes or steerable overtubes as described in U.S. Patent Application Publication No. 2010/0010299, incorporated herein by reference. Combinations of flexible endoscopes and steerable overtubes may also be used in some embodiments.

In at least one such embodiment, the endoscope 3214, a laparoscope, or a thoracoscope, for example, may be introduced into the patient trans-anally through the colon, the abdomen via an incision or keyhole and a trocar, or trans-orally through the esophagus or trans-vaginally through the cervix, for example. These devices may assist the clinician to guide and position the transection and sealing instrument 100 near the tissue treatment region to treat diseased tissue on organs such as the liver, for example.

In one embodiment, Natural Orifice Translumenal Endoscopic Surgery (NOTES)™ techniques may be employed to introduce the endoscope 3214 and various instruments into the patient and carry out the various procedures described herein. A NOTES™ technique is a minimally invasive therapeutic procedure that may be employed to treat diseased tissue or perform other therapeutic operations through a natural opening of the patient without making incisions in the abdomen. A natural opening may be the mouth, anus, and/or vagina. Medical implantable instruments may be introduced into the patient to the target area via the natural opening. In a NOTES™ technique, a clinician inserts a flexible endoscope into one or more natural openings of the patient to view the target area, for example, using a camera. During endoscopic surgery, the clinician inserts surgical devices through one or more lumens or working channels of the endoscope 3214 to perform various key surgical activities (KSA). These KSAs include forming an anastomosis between organs, performing dissections, repairing ulcers and other wounds. Although the devices and methods described herein may be used with NOTES™ techniques, it will be appreciated that they may also be used with other surgical techniques including, for example, other endoscopic techniques, and laparoscopic techniques.

It will be appreciated that the terms "proximal" and "distal" are used herein with reference to a clinician manipulating an end of an instrument extending from the clinician to a surgical site (e.g., through a trocar, through a natural orifice or through an open surgical site). The term "proximal" refers to the portion closest to the clinician, and the term "distal" refers to the portion located away from the clinician. It will be further appreciated that for conciseness and clarity, spatial terms such as "vertical," "horizontal," "up," and "down" may be used herein with respect to the drawings. However, surgical instruments are used in many orientations and positions, and these terms are not intended to be limiting and absolute.

While several embodiments have been illustrated and described, and while several illustrative embodiments have been described in considerable detail, the described embodiments are not intended to restrict or in any way limit the scope of the appended claims to such detail. Additional advantages and modifications may readily appear to those skilled in the art. Those of ordinary skill in the art will readily appreciate the different advantages provided by these various embodiments.

While several embodiments have been described, it should be apparent, however, that various modifications, alterations and adaptations to those embodiments may occur to persons skilled in the art with the attainment of some or all of the advantages of the embodiments. For example, according to various embodiments, a single component may be replaced by multiple components, and multiple components may be replaced by a single component, to perform a given function or functions. The described embodiments are therefore intended to cover all such modifications, alterations and adaptations without departing from the scope of the appended claims.

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and illustrative. Variations and changes thereto may be made without departing from the scope of the claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

The entire disclosures of the following non-provisional United States patents are hereby incorporated by reference herein:

U.S. Pat. No. 7,381,209, entitled ELECTROSURGICAL INSTRUMENT;
U.S. Pat. No. 7,354,440, entitled ELECTROSURGICAL INSTRUMENT AND METHOD OF USE;
U.S. Pat. No. 7,311,709, entitled ELECTROSURGICAL INSTRUMENT AND METHOD OF USE;
U.S. Pat. No. 7,309,849, entitled POLYMER COMPOSITIONS EXHIBITING A PTC PROPERTY AND METHODS OF FABRICATION;
U.S. Pat. No. 7,220,951, entitled SURGICAL SEALING SURFACES AND METHODS OF USE;
U.S. Pat. No. 7,189,233, entitled ELECTROSURGICAL INSTRUMENT;
U.S. Pat. No. 7,186,253, entitled ELECTROSURGICAL JAW STRUCTURE FOR CONTROLLED ENERGY DELIVERY;
U.S. Pat. No. 7,169,146, entitled ELECTROSURGICAL PROBE AND METHOD OF USE;
U.S. Pat. No. 7,125,409, entitled ELECTROSURGICAL WORKING END FOR CONTROLLED ENERGY DELIVERY;
U.S. Pat. No. 7,112,201, entitled ELECTROSURGICAL INSTRUMENT AND METHOD OF USE;
U.S. Patent Application Publication No. 2010/0010299, entitled ENDOSCOPIC TRANSLUMENAL ARTICULATABLE STEERABLE OVERTUBE; and
U.S. Patent Application Publication No. 2006/0111735, entitled CLOSING ASSEMBLIES FOR CLAMPING DEVICE.

Any patent, publication, or other disclosure material, in whole or in part, that is said to be incorporated by reference herein is incorporated herein only to the extent that the incorporated material does not conflict with existing definitions, statements or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of this application.

Preferably, the embodiments described herein will be processed before surgery. First a new or used instrument is obtained and, if necessary, cleaned. The instrument may then be sterilized. In one sterilization technique, the instrument is placed in a closed and sealed container, such as a plastic or TYVEK® bag. The container and instrument are then placed in a field of radiation that may penetrate the container, such as gamma radiation, x-rays, or higher energy electrons. The radiation kills bacteria on the instrument and in the container. The sterilized instrument may then be stored in the sterile container. The sealed container keeps the instrument sterile until it is opened in the medical facility.

The embodiments are not to be construed as limited to the particular embodiments disclosed. The embodiments are therefore to be regarded as illustrative rather than restrictive. Variations and changes may be made by others without departing from the scope of the claims. Accordingly, it is expressly intended that all such equivalents, variations and changes that fall within the scope of the claims be embraced thereby.

In summary, numerous benefits have been described which result from employing the embodiments described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical applications to thereby enable one of ordinary skill in the art to utilize the various embodiments and with various modifications as are suited to the particular use contemplated. It is intended that the claims submitted herewith define the overall scope.

What is claimed is:

1. A surgical instrument comprising:
    a shaft extending along a longitudinal axis;
    an end effector, comprising:
        a first jaw member defining a first longitudinal slot;
        a second jaw member defining a second longitudinal slot, wherein, in an open position, the first jaw member and the second jaw member are arranged parallel to and offset from the longitudinal axis; and
        a first push rod member having a distally directed end pivotably coupled to the first jaw member and a proximally directed end pivotably coupled at a first pivot point; and
    a reciprocatable member translatable distally and proximally through the first longitudinal slot and the second longitudinal slot, wherein the reciprocatable member comprises:
        a blade at a distal portion of the reciprocatable member;
        a transverse element positioned to pass through the first longitudinal slot; and
        a first shoulder element coupled to and substantially perpendicular to the transverse element;
    wherein the first shoulder element is configured to slidably contact the first jaw member to cause the first push rod member to pivot about the first pivot point such that the first jaw member translates toward the second jaw member in a substantially parallel motion.

2. The surgical instrument of claim 1, wherein the end effector further comprises a second push rod member having a distally directed end pivotably coupled to the second jaw member and a proximally directed end pivotably coupled at the first pivot point, wherein the reciprocatable member further comprises a second shoulder element coupled to the transverse element opposite the first shoulder element, and wherein the second shoulder element is configured to slidably contact the second jaw member to cause the second push rod member to pivot about the first pivot point such that the second jaw member translates toward the first jaw member in a substantially parallel motion.

3. The surgical instrument of claim 2, wherein the end effector further comprises:
a third push rod member having a distally directed end pivotably coupled to the first jaw member and a proximally directed end pivotably coupled at a second pivot point; and
a fourth push rod member having a distally directed end pivotably coupled to the second jaw member and a proximally directed end pivotably coupled at the second pivot point.

4. The surgical instrument of claim 1, further comprising a first linkage member having a distally directed end pivotably coupled to the second jaw member at the first pivot point.

5. The surgical instrument of claim 1, wherein the end effector is coupled to a distal end of the shaft.

6. The surgical instrument of claim 5, wherein the first push rod member of the end effector is pivotably coupled to the shaft at the first pivot point.

7. The surgical instrument of claim 5, further comprising a clevis coupled to a distal portion of the shaft, and wherein the first push rod member of the end effector is pivotably coupled to the clevis at the first pivot point.

8. The surgical instrument of claim 5, wherein the first push rod member is positioned between the first jaw member and an interior portion of the shaft.

9. The surgical instrument of claim 1, wherein the second jaw member is coupled to the shaft.

10. The surgical instrument of claim 1, wherein the first jaw member is configured to further translate distally while it translates towards the second jaw member in the substantially parallel motion.

11. The surgical instrument of claim 1, wherein the first push rod member is positioned substantially proximal relative to the first and second jaw members.

12. The surgical instrument of claim 1, wherein the transverse element of the reciprocatable member defines a longitudinal slot arranged to accommodate the first pivot point during translation of the reciprocatable member.

13. The surgical instrument of claim 1, wherein the end effector further comprises a second push rod member having a distally directed end pivotably coupled to the first jaw member and a proximally directed end pivotably coupled to a second pivot point, and wherein the first shoulder element is configured to slidably contact the first jaw member to further cause the second push rod member to pivot about the second pivot point such that the first jaw member translates toward the second jaw member in a substantially parallel motion.

14. The surgical instrument of claim 1, wherein the end effector further comprises at least one electrode for treating tissue located between the first jaw member and the second jaw member.

15. A surgical instrument defining a parallel-closing jaw, the surgical instrument comprising:
a first jaw member defining a first longitudinal slot;
a second jaw member defining a second longitudinal slot, wherein, in an open position, the first jaw member is positioned parallel to and offset from the second jaw member;
a first push rod member having a distally directed end pivotably coupled to the first jaw member and a proximally directed end pivotably coupled at a first pivot point; and
a reciprocatable member translatable distally and proximally through the first longitudinal slot and the second longitudinal slot, wherein the reciprocatable member comprises:
a blade at a distal portion of the reciprocatable member;
a transverse element positioned to pass through the first longitudinal slot; and
a first flange coupled to and substantially perpendicular to the transverse element;
wherein the first flange is configured to interact with the first jaw member, during distal translation of the reciprocatable member, to cause the first push rod member to rotate about the first pivot point such that the first jaw member translates toward the second jaw member in a substantially parallel motion.

16. The surgical instrument of claim 15, further comprising a first linkage member having a distally directed end pivotably coupled to the first jaw member and a proximally directed end pivotably coupled at a second pivot point.

17. The surgical instrument of claim 15, further comprising a shaft, wherein the first jaw member and the second jaw member are coupled to a distal end of the shaft.

18. The surgical instrument of claim 15, further comprising a second push rod member having a distally directed end pivotably coupled to the second jaw member and a proximally directed end pivotably coupled at the first pivot point.

19. The surgical instrument of claim 18, further comprising:
a third push rod member having a distally directed end pivotably coupled to the first jaw member and a proximally directed end pivotably coupled at a second pivot point; and
a fourth push rod member having a distally directed end pivotably coupled to the second jaw member and a proximally directed end pivotably coupled at the second pivot point.

20. The surgical instrument of claim 16, further comprising a second linkage member having a distally directed end pivotably coupled to the second jaw member and a proximally directed end pivotably coupled at the second pivot point.

* * * * *